United States Patent
Sun et al.

(10) Patent No.: US 10,456,479 B2
(45) Date of Patent: Oct. 29, 2019

(54) HYDROPHILIC LINKERS AND LIGAND-DRUG CONJUGATES THEREOF

(71) Applicant: HANGZHOU DAC BIOTECH CO., LTD., Hangzhou (CN)

(72) Inventors: Sanxing Sun, Hangzhou (CN); Robert Yongxin Zhao, Hangzhou (CN); Xing Li, Hangzhou (CN); Huihui Guo, Hangzhou (CN); Junxiang Jia, Hangzhou (CN); Hongsheng Xie, Hangzhou (CN); Xiaomai Zhou, Hangzhou (CN); Yuanyuan Huang, Hangzhou (CN); Qingliang Yang, Hangzhou (CN); Xiaotao Zhuo, Hangzhou (CN); Hangbo Ye, Hangzhou (CN); Shun Gai, Hangzhou (CN); Lan Qu, Hangzhou (CN); Wenjun Li, Hangzhou (CN); Chen Lin, Hangzhou (CN)

(73) Assignee: HANGZHOU DAC BIOTECH CO., LTD., Hangzhou (CN)

( * ) Notice: Subject to any disclaimer, the term of this patent is extended or adjusted under 35 U.S.C. 154(b) by 0 days.

(21) Appl. No.: 15/558,917

(22) PCT Filed: Mar. 19, 2015

(86) PCT No.: PCT/IB2015/052011
§ 371 (c)(1),
(2) Date: Sep. 15, 2017

(87) PCT Pub. No.: WO2016/147031
PCT Pub. Date: Sep. 22, 2016

(65) Prior Publication Data
US 2018/0110876 A1   Apr. 26, 2018

(51) Int. Cl.
| A61K 47/68 | (2017.01) |
| C07D 207/46 | (2006.01) |
| C07F 9/6558 | (2006.01) |
| C07K 16/00 | (2006.01) |
| C07K 16/28 | (2006.01) |

(52) U.S. Cl.
CPC ...... A61K 47/6889 (2017.08); A61K 47/6803 (2017.08); A61K 47/6811 (2017.08); A61K 47/6849 (2017.08); A61K 47/6851 (2017.08); C07D 207/46 (2013.01); C07F 9/65583 (2013.01); C07K 16/00 (2013.01); C07K 16/2878 (2013.01)

(58) Field of Classification Search
CPC ............ A61K 47/6889; A61K 47/6811; A61K 47/6851; A61K 47/6803; A61K 47/6849; C07D 207/46; C07F 9/572; C07F 9/65583; C07K 16/00; C07K 16/2878
USPC ........................................................ 548/400
See application file for complete search history.

(56) References Cited

U.S. PATENT DOCUMENTS

| 2013/0066055 A1 | 3/2013 | Lerchen et al. |
| 2013/0095123 A1 | 4/2013 | Lerchen et al. |
| 2013/0122024 A1 | 5/2013 | Lerchen et al. |
| 2013/0144541 A1 | 6/2013 | Rychnovsky et al. |
| 2014/0127240 A1 | 5/2014 | Lerchen et al. |
| 2015/0030618 A1 | 1/2015 | Lerchen et al. |
| 2015/0246136 A1 | 9/2015 | Lerchen et al. |
| 2015/0250896 A1 | 9/2015 | Zhao |
| 2016/0193359 A1 | 7/2016 | Lerchen et al. |
| 2018/0110876 A1 | 4/2018 | Sun et al. |

FOREIGN PATENT DOCUMENTS

| WO | 2006/107175 A1 | 10/2006 |
| WO | WO 2010/126551 A1 | 11/2010 |
| WO | WO 2012/143497 A2 | 10/2012 |
| WO | WO 2014/080251 A1 | 5/2014 |
| WO | 2014/151030 A1 | 9/2014 |
| WO | 2015/028850 A1 | 3/2015 |

OTHER PUBLICATIONS

International Search Report (PCT/ISA/210) dated Jan. 25, 2016, by the State Intellectual Property Office of the P. R. China as the International Searching Authority for International Application No. PCT/IB2015/052011.
Written Opinion (PCT/ISA/237) dated Jan. 25, 2016, by the State Intellectual Property Office of the P. R. China as the International Searching Authority for International Application No. PCT/IB2015/052011.
Szakács et al., Targeting multidrug resistance in cancer, *Nature Reviews Drug Discovery*, Mar. 2006, pp. 219-234, vol. 5, Nature Publishing Group. DOI:10.1038/nrd1984.
Leonard et al., The Role of ABC Transporters in Clinical Practice, *The Oncologist*, 2003, vol. 8, pp. 411-424, AlphaMed Press. PMID:14530494.
Takeshita et al., CMC-544 (inotuzumab ozogamicin) shows less effect on multidrug resistant cells: analyses in cell lines and cells from patients with B-cell chronic lymphocytic leukaemia and lymphoma, *British Journal of Haematology*, Apr. 20, 2009, pp. 34-43, vol. 146, Blackwell Publishing Ltd. DOI:10.1111/j.1365-2141.2009.07701.x.

(Continued)

*Primary Examiner* — Kristin A Vajda
(74) *Attorney, Agent, or Firm* — Buchana Ingersoll & Rooney PC

(57) ABSTRACT

Hydrophilic linkers are useful for linking drugs to cell-binding ligands in ligand-drug conjugates, such as antibody-drug conjugates. The ligand-drug conjugate includes a cell-binding ligand capable of binding to a particular cell population, and a drug connected to the ligand by a hydrophilic linker. The hydrophilic linker includes one or more hydrophilic groups that render the linker hydrophilic. The hydrophilic linker may also include functional groups at the two termini for coupling to the drug and the cell-binding ligand respectively.

26 Claims, 1 Drawing Sheet

(56) References Cited

OTHER PUBLICATIONS

Sharom, ABC multidrug transporters: Structure, function and role in chemoresistance, *Pharmacogenomics*, Feb. 2008, pp. 105-127, PubMed. DOI:10.2217/14622416.9.1.105.

Lehne, P-glycoprotein as a Drug Target in the Treatment of Multidrug Resistant Cancer, *Current Drug Targets*, 2000, pp. 85-99, vol. 1, No. 1, Bentham Science Publishers Ltd.

Guillemard et al., Prodrug chemotherapeutics bypass p-glycoprotein resistance and kill tumors in vivo with high efficacy and target-dependent selectivity, *Oncogene*, Mar. 22, 2004, pp. 3613-3621, vol. 23, Nature Publishing Group. DOI:10.1038/sj.onc.1207463.

Takara et al., An update on overcoming MDR1-mediated multidrug resistance in cancer chemotherapy, *Current Pharmaceutical Design*, 2006, pp. 273-286, vol. 12, No. 3. PMID:16454744. (Abstract only).

Hamann et al., An anti-MUC1 antibody-calicheamicin conjugate for treatment of solid tumors. Choice of linker and overcoming drug resistance., *Bioconjugate Chemistry*, Mar.-Apr. 2005, pp. 346-353, vol. 16, No. 2, American Chemical Society. DOI:10.1021/bc049795f. (Abstract only).

Examination Report No. 1 dated May 11, 2018, by the Australian Patent Office in corresponding Australian Patent 4pplication No. 2015386647. (4 pages).

Notification Concerning Transmittal of International Preliminary Report on Patentability and the Written Opinion of the International Searching Authority (Forms PCT/IB/326, PCT/IB/373, and PCT/ISA/237) dated Sep. 28, 2017 by the International Bureau of WIPO in corresponding International Application No. PCT/IB2015/052011. (6 pages).

The extended European search report dated Mar. 28, 2019, by the European Patent Office in corresponding European Patent Application No. 15885301.0. (12 pages).

Office Action dated Aug. 1, 2019, by the U.S. Patent and Trademark Office in related U.S. Appl. No. 16/226,093. (10 pages).

Ilyin et al., "One-Step Construction of Peptidomimetic 5-Carbamoyl-4-sulfonyl-2-piperazinones," Journal of Combinatorial Chemistry, (Oct. 2005), vol. 3, No. 3, pp. 360-363.

Office Action dated Feb. 5, 2019, by the U.S. Patent and Trademark Office in related U.S. Appl. No. 16/226,093. (7 pages).

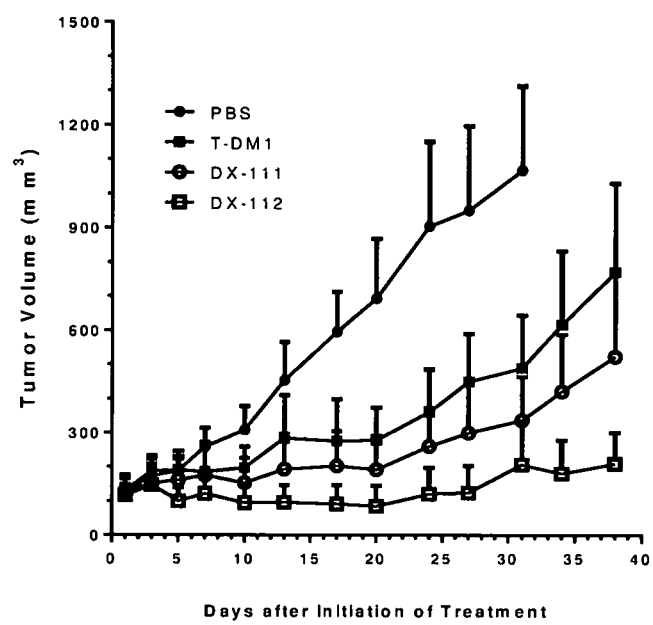

HYDROPHILIC LINKERS AND LIGAND-DRUG CONJUGATES THEREOF

FIELD OF THE INVENTION

The present invention relates to novel hydrophilic linkers that are useful for linking drugs (e.g., cytotoxic drugs) to cell-binding ligands (e.g., antibodies). The use of the hydrophilic linkers of the invention increases the potency and therapeutic index of the ligand-drug conjugates (e.g., antibody-drug conjugates). This is particularly effective when the hydrophilic linkers are used as non-cleavable ones. The present invention further relates to methods for preparing the novel hydrophilic linkers and the ligand-drug conjugates thereof.

BACKGROUND OF THE INVENTION

In order to reduce systemic toxicities, a promising approach to achieve targeted delivery of cytotoxic drugs to tumor cells is to use antibody-drug conjugates (ADCs) or other types of ligand-drug conjugates as self-guided tumor-targeting drugs. Antibody-drug conjugates, which combine the specificity of monoclonal antibodies and the potency of cytotoxic drugs, have been under intense pursuit for over 30 years. The recent approval of two ADCs, brentuximab vedotin for the treatment of Hodgkin's lymphoma and ado-trastuzumab emtansine for the treatment of metastatic breast cancer, has boosted the research activities in the field to a new level. It has become common for a biotech or pharmaceutical company to have programs in the field of antibody-drug conjugates.

However, even with ADCs, an old problem still exists. It is known that after multiple treatments of cancer patients with chemotherapeutic drugs, the patients may become resistant to such treatment (Szakacs et al. Nat Rev Drug Discov. 2006, 5: 219-34). There are several mechanisms by which tumor cells can become resistant. Among them the multidrug-resistant (MDR) proteins are important membrane pumps that can transport chemotherapeutic agents out of the cells. One of the more prevalent MDR pumps is MDR1. The MDR1, which is also known as P-glycoprotein 1 (PGP1) or ATP-binding cassette sub-family B member 1 (ABCB 1), is the most common efflux pump of anticancer drugs, and correlations between MDR1 expression and poor responses to chemotherapy have been demonstrated for many cancer types (Takara et al. Curr Pharm Des 2006, 12: 273-86; Leonard et al. Oncologist 2003, 8: 411-24). Yet, the majority of cytotoxic drugs that have been used in ADCs, such as maytansinoids, dolastatins, calicheamicin, doxorubicin, taxanes, and duocarmycins, are also substrates of the MDR1 transporter, and the activity of many ADCs is poor in MDR1-expressing cells (Takeshita et al. Br J Haematol. 2009, 146, 34-43; Hamann et al. Bioconjug Chem. 2005, 16, 346-53).

MDR1 causes resistance to chemotherapeutic drugs via two mechanisms. First, by effluxing drugs that have diffused into the plasma membrane from extracellular spaces. In such cases, the compounds are prevented from entering the cytoplasm. Second, by effluxing compounds that have entered the cytoplasm to the outside of the cell (Sharom. Pharmacogenomics. 2008, 9, 105-27; Lehne. Curr Drug Targets. 2000, 1, 85-99). Due to that ADCs deliver the cytotoxic drugs to the cytoplasm via antigen-mediated endocytosis, the first type of resistence is prevented (Hamann et al. Bioconjug Chem. 2005, 16, 346-53; Guillemard et al. Oncogene. 2004, 23, 3613-21). However, after the conjugates are processed into small fragments inside the cells, the cytotoxic drugs are still susceptible to the second type of resistance, i.e., the effluxing of drugs from the cytoplasm to extracellular spaces.

For ADCs, the MDR1 not only decreases the potency of cytotoxic drugs, but also decreases the therapeutic index, because once transported to the extracellular spaces by MDR1, the cytotoxic drugs may also cause damage to normal healthy cells of the body. It can significantly compromise the results of the targeted antitumor therapies.

Therefore, even with antibody-drug conjugates, there is still a need to overcome the problem of multidrug resistance. This will help increase the potency and therapeutic index of antibody-drug conjugates, and enable antibody-drug conjugates to achieve the intended goal of targeted antitumor therapy on a much higher level.

SUMMARY OF THE INVENTION

The present invention improves the potency and therapeutic index of ligand-drug conjugates by using hydrophilic linkers that incorporate a variety of polar or charged groups.

The ligand-drug conjugates made from the hydrophilic linkers are highly potent toward tumor cells.

The general formula of the hydrophilic linkers of the present invention is shown in Formula (1):

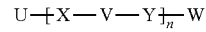

Formula 1 wherein:

V represents a polar or charged group; Suitable polar or charged groups that can be used in Formula (1) include, but are not limited to, aminos [—N(R)—], ureas [—N(R$_1$)CON(R$_2$)— or —N(CONR$_1$R$_2$)—], carboxyls [-Q(COOH)— or -Q(ZCOOH)—], carbamates {[—N(R)COO—] or [—N(COOR)—]}, guanidines [—N(R$_1$)C=N(COOR$_2$)N(R$_3$)—], sulfonamides [—N(SO$_2$R)—], sulfones (—SO$_2$—), sulfoxides (—SO—), sulfonic acids [-Q(ZSO$_2$OH)—], sulfamic acids [—N(SO$_2$OH)—], phosphonates {-Q[ZPO(OR)$_2$]—}, phosphonic acids {-Q[ZPO(OH)$_2$]—}, phosphoramidic acids {—N[PO(OH)$_2$]—}, phosphorodiamidic acids {—N[PO(NH$_2$)(OH)]—}, and phosphoric triamides {—N[PO(NH$_2$)$_2$]—}, wherein R, R$_1$, R$_2$ and R$_3$ are independently H or C$_1$~C$_8$ alkyl; Q is CH or N; Z is 1~5 methylene units.

U represents a reactive functional group that enables a covalent linkage with a cytotoxic drug; The reactive functional groups that enable a covalent linkage with a cytotoxic drug include, but are not limited to, thiols, disulfides, aminos, carboxyls, aldehydes, ketones, maleimides, haloacetyl groups, alkenyl groups, alkynyl groups, hydrazines, and hydroxyls. The covalent linkage with the cytotoxic drug can be a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, or a carbonate linkage;

W represents a reactive functional group that enables a covalent linkage with a cell-binding ligand, such as a monoclonal antibody. The functional groups that enable a covalent linkage with a cell-binding ligand mainly include two types. The first type of functional groups enable a covalent linkage with an amino group on the cell-binding ligand. These functional groups include, but are not limited to, N-hydroxysuccinmide esters, N-sulfosuccinimidyl esters, nitrophenyl esters, dinitrophenyl esters, pentafluorophenyl esters, tetrafluorophenyl esters, acyl chlorides, anhydrides, sulfonyl chlorides, chloroformates, isocyanates, isothiocyanates, aldehydes, and ketones. The covalent linkage can be an amide linkage, a carbamate linkage, a urea linkage, or other types of carbon-nitrogen bonds. The second type of functional groups enable a covalent linkage with a thiol group on the cell-binding ligand. These functional groups include, but are not limited to, disulfides such as pyridyldisulfides and nitropyridyldisulfides, maleimides, acyl chlorides, haloacetyl groups such as iodoacetamide and bromoacetamide, alkenyl pyridines, isocyanates, and isothiocyanates. The covalent linkage can be a disulfide linkage, a thioether linkage, a thiocarbamate linkage, a dithiocarbamate linkage, or a thioester linkage;

X represents a component composed of one, two, or three methylene units. The methylene units can be optionally substituted with alkyl, halo, hydroxyl, or alkoxy groups;

Y represents a component composed of one, two, or three methylene units. The methylene units can be optionally substituted with alkyl, halo, hydroxyl, or alkoxy groups;

n is an integer from 1 to 100. If n>1, the values of each V, X, and Y in the repeating brackets of Formula (1) are independent and do not have to be identical.

Preferably n is an integer from 1 to 50. Even more preferably, n is an integer from 1 to 10. Most preferably n is an integer from 1 to 4.

A further aspect of the present invention relates to novel ligand-drug conjugates. The present invention provides ligand-drug conjugates comprising a cell-binding ligand that binds to a particular cell population, a cytotoxic drug that is highly potent, and a hydrophilic linker that connects the cell-binding ligand and the cytotoxic drug. The ligand-drug conjugates of the present invention have superior efficacy and safety than ligand-drug conjugates comprising nonhydrophilic linkers.

The general formula of the antibody-drug conjugates of the present invention is shown in Formula (2):

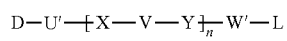

Formula 2 wherein:

D represents a cytotoxic drug;

L represents a cell-binding ligand;

V represents a polar or charged group; Suitable polar or charged groups that can be used in Formula (2) include, but are not limited to, aminos [—N(R)—], ureas [—N($R_1$)CON($R_2$)— or —N(CON$R_1R_2$)—], carboxyls [-Q(COOH)— or -Q(ZCOOH)—], carbamates {[—N(R)COO—] or [—N(COOR)—]}, guanidines [—N($R_1$)C=N(COO$R_2$)N($R_3$)—], sulfonamides [—N(SO$_2$R)—], sulfones (—SO$_2$—), sulfoxides (—SO—), sulfonic acids [-Q(ZSO$_2$OH)—], sulfamic acids [—N(SO$_2$OH)—], phosphonates {-Q[ZPO(OR)$_2$]—}, phosphonic acids {-Q[ZPO(OH)$_2$]—}, phosphoramidic acids {—N[PO(OH)$_2$]—}, phosphorodiamidic acids {—N[PO(NH$_2$)(OH)]—}, and phosphoric triamides {—N[PO(NH$_2$)$_2$]—}, wherein R, $R_1$, $R_2$ and $R_3$ are independently H or $C_1$~$C_8$ alkyl; Q is CH or N; Z is 1~5 methylene units.

U' represents a functional group that enables a covalent linkage with a cytotoxic drug; The functional groups that enable a covalent linkage with a cytotoxic drug include, but are not limited to, thiols, disulfides, aminos, carboxyls, aldehydes, ketones, maleimides, haloacetyl groups, alkenyl groups, alkynyl groups, hydrazines, and hydroxyls. The covalent linkage with the cytotoxic drug can be a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, or a carbonate linkage;

W' represents a functional group that enables a covalent linkage with a cell-binding ligand, such as a monoclonal antibody. The functional groups that enable a covalent linkage with a cell-binding ligand mainly include two types. The first type of functional groups enable a covalent linkage with an amino group on the cell-binding ligand. These functional groups include, but are not limited to, N-hydroxysuccinmide esters, N-sulfosuccinimidyl esters, nitrophenyl esters, dinitrophenyl esters, pentafluorophenyl esters, tetrafluorophenyl esters, acyl chlorides, anhydrides, sulfonyl chlorides, chloroformates, isocyanates, isothiocyanates, aldehydes, and ketones. The covalent linkage can be an amide linkage, a carbamate linkage, a urea linkage, or other types of carbon-nitrogen bonds. The second type of functional groups enable a covalent linkage with a thiol group on the cell-binding ligand. These functional groups include, but are not limited to, disulfides such as pyridyldisulfides and nitropyridyldisulfides, maleimides, acyl chlorides, haloacetyl groups such as iodoacetamide and bromoacetamide, alkenyl pyridines, isocyanates, and isothiocyanates. The covalent linkage can be a disulfide linkage, a thioether linkage, a thiocarbamate linkage, a dithiocarbamate linkage, or a thioester linkage;

X represents a component composed of one, two, or three methylene units. The methylene units can be optionally substituted with alkyl, halo, hydroxyl, or alkoxy groups;

Y represents a component composed of one, two, or three methylene units. The methylene units can be optionally substituted with alkyl, halo, hydroxyl, or alkoxy groups;

n is an integer from 1 to 100. If n>1, the values of each V, X, and Y in the repeating brackets of Formula (2) are independent and do not have to be identical.

Preferably n is an integer from 1 to 50. Even more preferably, n is an integer from 1 to 10. Most preferably n is an integer from 1 to 4.

BRIEF DESCRIPTION OF THE DRAWINGS

FIG. 1 shows the in vivo test results of three antibody-drug conjugates in a target-positive xenograft tumor model.

DETAILED DESCRIPTION OF THE INVENTION

Although MDR1 effluxes a great variety of compounds, generally speaking, MDR1 preferentially transport hydrophobic compounds and most of the MDR1 substrates are hydrophobic (Loo et al. J Membr Biol. 2005, 206, 173-85). The hydrophilic compounds are usually much less susceptive to MDR1-mediated efflux and can be mostly retained inside the cells. Accordingly, the inclusion of hydrophilic groups in drug molecules has often been used as a way to combat MDR1 and overcome multidrug reststance (Szokacs et al. Nature Reviews. 5, 219-235, 2006; Kovtun et al. Cancer Res. 2010, 70, 2528-2537; Zhao et al. J. Med. Chem. 2011, 54, 3606-3623).

The present invention circumvent the problem of multidrug resistance by using hydrophilic linkers to construct antibody-drug conjugates. The hydrophilic linker bestows the ability to overcome MDR1-mediated resistance to the linked cytotoxic drug. This is particularly effective when the hydrophilic linker is used as a non-cleavable one, because the hydrophilic linker will always remain connected to the cytotoxic drug (Szakacs et al. Nature Reviews Drug Discovery. 2006, 5: 219-234). As a result, the hydrophilicity of the linker can permanently make the linked cytotoxic drug more resistant to MDR1-mediated efflux. It will keep the linked cytotoxic drug retained inside the target cell and exert its cytotoxic effect.

Furthermore, a highly hydrophilic linker can also circumvent the problem that some antibody-drug conjugates may undergo aggregation, due to the hydrophobicity of either the linker or the cytotoxic drug, or both (Jeffrey et al. J Med Chem. 2005, 48: 1344-1358). By increasing the solubility of the antibody-drug conjugates, a highly hydrophilic linker effectively minimizes the problem. In addition, it also allows the incorporation of a relatively large number of drugs on each antibody, thereby increasing the potency of the antibody-drug conjugates even further (Zhao et al. J. Med. Chem. 2011, 54, 3606-3623).

The Hydrophilic Linkers

In one aspect of the invention, the present invention improves the potency and therapeutic index of ligand-drug conjugates by using hydrophilic linkers that incorporate a variety of polar or charged groups. The ligand-drug conjugates, such as antibody-drug conjugates, made from such hydrophilic linkers are highly potent toward multidrug resistant tumor cells.

The general formula of the hydrophilic linkers of the present invention is shown in Formula (1):

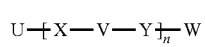

Formula 1 wherein:

V represents a polar or charged group; Suitable polar or charged groups that can be used in Formula (1) include, but are not limited to, aminos [—N(R)—], ureas [—N($R_1$)CON($R_2$)— or —N(CON$R_1R_2$)—], carboxyls [-Q(COOH)— or -Q(ZCOOH)—], carbamates {[—N(R)COO—] or [—N(COOR)—]}, guanidines [—N($R_1$)C=N(COO$R_2$)N($R_3$)—], sulfonamides [—N($SO_2$R)—], sulfones (—$SO_2$—), sulfoxides (—SO—), sulfonic acids [-Q(Z$SO_2$OH)—], sulfamic acids [—N($SO_2$OH)—], phosphonates {-Q[ZPO(OR)$_2$]—}, phosphonic acids {-Q[ZPO(OH)$_2$]—}, phosphoramidic acids {—N[PO(OH)$_2$]—}, phosphorodiamidic acids {—N[PO(N$H_2$)(OH)]—}, and phosphoric triamides {—N[PO(N$H_2$)$_2$]—}, wherein R, $R_1$, $R_2$ and $R_3$ are independently H or $C_1$~$C_8$ alkyl; Q is CH or N; Z is 1~5 methylene units.

U represents a reactive functional group that enables a covalent linkage with a cytotoxic drug; The reactive functional groups that enable a covalent linkage with a cytotoxic drug include, but are not limited to, thiols, disulfides, aminos, carboxyls, aldehydes, ketones, maleimides, haloacetyl groups, alkenyl groups, alkynyl groups, hydrazines, and hydroxyls. The covalent linkage with the cytotoxic drug can be a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, or a carbonate linkage;

W represents a reactive functional group that enables a covalent linkage with a cell-binding ligand, such as a monoclonal antibody. The functional groups that enable a covalent linkage with a cell-binding ligand mainly include two types. The first type of functional groups enable a covalent linkage with an amino group on the cell-binding ligand. These functional groups include, but are not limited to, N-hydroxysuccinmide esters, N-sulfosuccinimidyl esters, nitrophenyl esters, dinitrophenyl esters, pentafluorophenyl esters, tetrafluorophenyl esters, acyl chlorides, anhydrides, sulfonyl chlorides, chloroformates, isocyanates, isothiocyanates, aldehydes, and ketones. The covalent linkage can be an amide linkage, a carbamate linkage, a urea linkage, or other types of carbon-nitrogen bonds. The second type of functional groups enable a covalent linkage with a thiol group on the cell-binding ligand. These functional groups include, but are not limited to, disulfides such as pyridyldisulfides and nitropyridyldisulfides, maleimides, acyl chlorides, haloacetyl groups such as iodoacetamide and bromoacetamide, alkenyl pyridines, isocyanates, and isothiocyanates. The covalent linkage can be a disulfide linkage, a thioether linkage, a thiocarbamate linkage, a dithiocarbamate linkage, or a thioester linkage;

X represents a component composed of one, two, or three methylene units. The methylene units can be optionally substituted with alkyl, halo, hydroxyl, or alkoxy groups;

Y represents a component composed of one, two, or three methylene units. The methylene units can be optionally substituted with alkyl, halo, hydroxyl, or alkoxy groups;

n is an integer from 1 to 100. If n>1, the values of each V, X, and Y in the repeating brackets of Formula (1) are independent and do not have to be identical.

As exemplary embodiments of the invention, Compound (1) to (15) are some of the hydrophilic linkers that can be used to prepare the ligand-drug conjugates of the present invention.

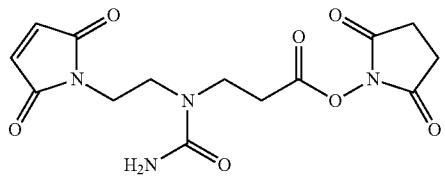

(Compound 1)

In Compound (1), the urea group in the middle of the linker renders the linker hydrophilic. The maleimide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester, which is often used as a reactive functional group to activate carboxylic acids, can react with the amino groups on the ligand or drug to form a stable amide bond.

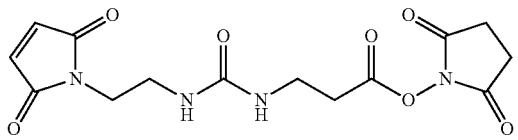

(Compound 2)

In Compound (2), the urea group in the middle of the linker renders the linker hydrophilic. The maleimide group at the left terminus of the linker is used as an anchor to attach to ligand or drug molecules. The maleimide group readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 3)

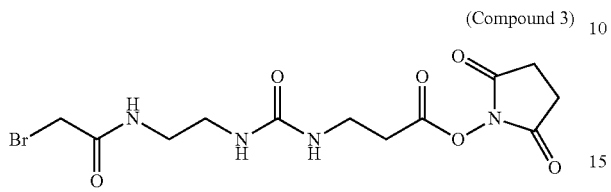

In Compound (3), the urea group in the middle of the linker renders the linker hydrophilic. The bromoacetamide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 4)

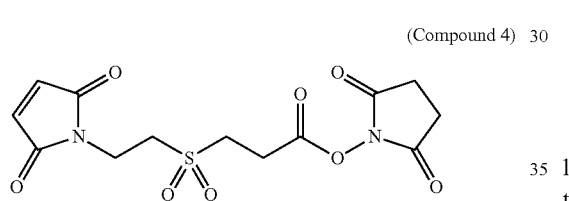

In Compound (4), the sulfone group in the middle of the linker renders the linker hydrophilic. The maleimide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 5)

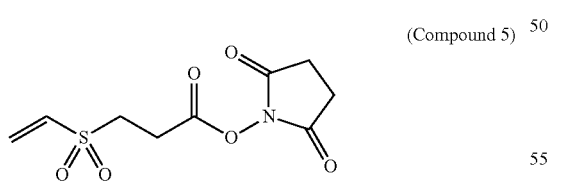

In Compound (5), the sulfone group in the middle of the linker renders the linker hydrophilic. The alkenyl group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 6)

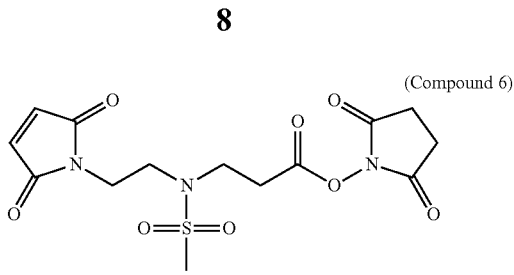

In Compound (6), the sulfonamide group in the middle of the linker renders the linker hydrophilic. The maleimide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 7)

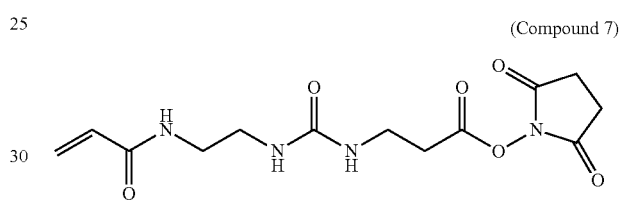

In Compound (7), the urea group in the middle of the linker renders the linker hydrophilic. The alkenyl group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 8)

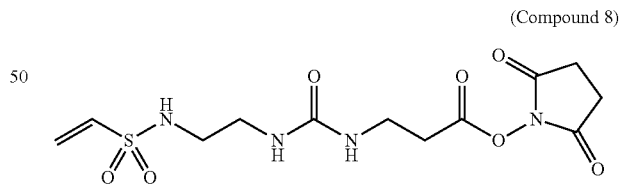

In Compound (8), the urea group and the sulfonamide group in the middle of the linker renders the linker hydrophilic. The alkenyl group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 9)

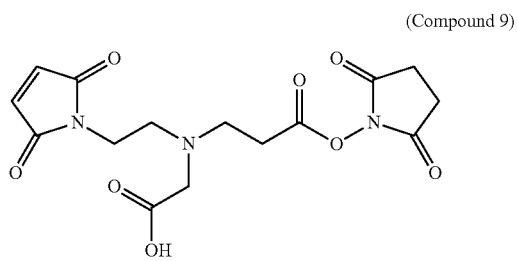 [SMILES: O=C(O)CN(CCC(=O)ON1C(=O)CCC1=O)CCN1C(=O)C=CC1=O]

In Compound (9), the glycine group in the middle of the linker renders the linker hydrophilic. The maleimide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 10)

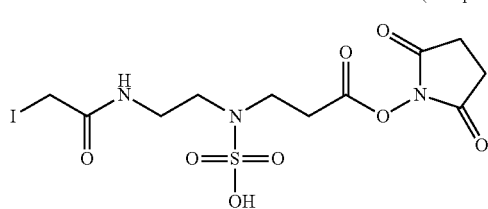

In Compound (10), the sulfamic acid group in the middle of the linker renders the linker hydrophilic. The iodoacetamide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 11)

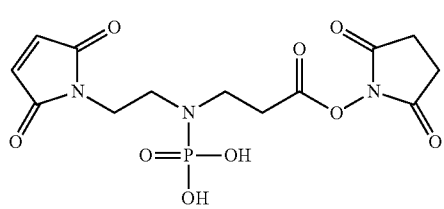

In Compound (11), the phosphoramidic acid group in the middle of the linker renders the linker hydrophilic. The maleimide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 12)

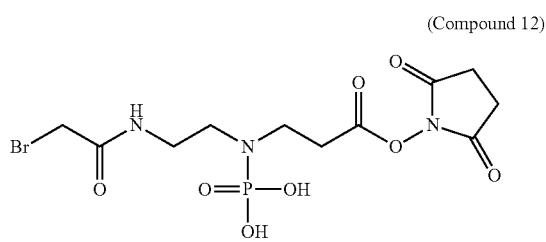 [SMILES: O=C(CBr)NCCN(CCC(=O)ON1C(=O)CCC1=O)P(=O)(O)O]

In Compound (12), the phosphoramidic acid group in the middle of the linker renders the linker hydrophilic. The bromoacetamide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 13)

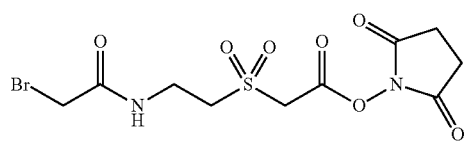

In Compound (13), the sulfone group and the amide group in the middle of the linker renders the linker hydrophilic. The bromoacetamide group at the left terminus of the linker is used as an anchor to link to ligand or drug molecules. It readily reacts with the thiol groups on the ligand or thiol-containing drug to form a stable thioether bond. The N-hydroxysuccinimide ester (NHS ester) at the right terminus of the linker is also used to link to ligand or drug molecules. The NHS ester can react with the amino groups on the ligand or drug to form a stable amide bond.

(Compound 14)

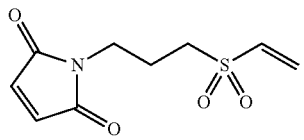

In Compound (14), the sulfone group in the middle of the linker renders the linker hydrophilic. The maleimide group at the left terminus of the linker is used as an anchor to link to ligand or drug molecules. It readily reacts with the thiol groups on the ligand or thiol-containing drug to form a stable thioether bond. The alkenyl group at the right terminus of the linker is used as an anchor to link to ligand or drug molecules. It readily reacts with the thiol groups on the ligand or thiol-containing drug to form a stable thioether bond.

(Compound 15)

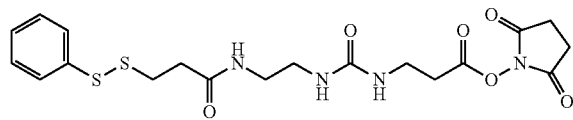

In Compound (15), the urea group and the amide group in the middle of the linker renders the linker hydrophilic. The disulfide group at the left terminus of the linker is used as an anchor to attach to ligand or drug molecules. The disulfide group readily reacts with the thiol groups on the ligand or thiol-containing drug to form a new disulfide bond. The N-hydroxysuccinimide ester (NHS ester) at the right terminus of the linker is also used to link to ligand or drug molecules. The NHS ester can react with the amino groups on the ligand or drug to form a stable amide bond.

More exemplary hydrophilic linkers are shown in the structures below [Compounds (16) to (26)]:

(Compound 16)

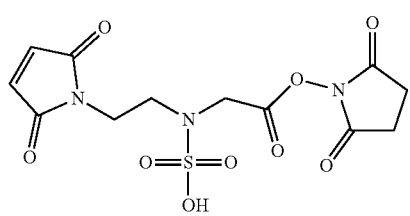

(Compound 17)

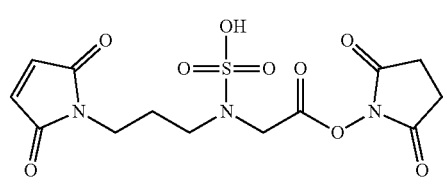

(Compound 18)

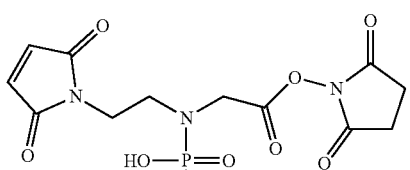

(Compound 19)

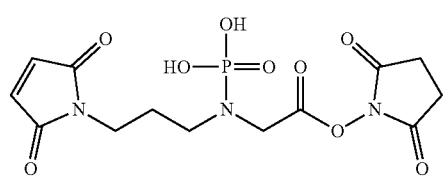

(Compound 20)

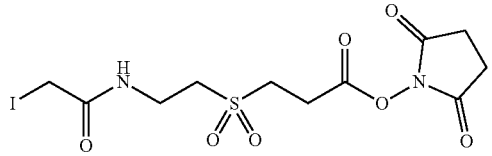

(Compound 21)

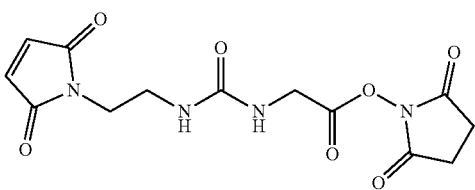

(Compound 22)

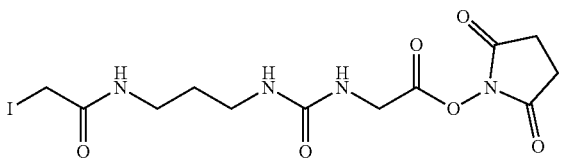

(Compound 23)

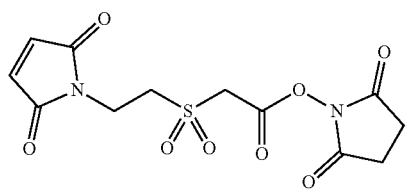

(Compound 24)

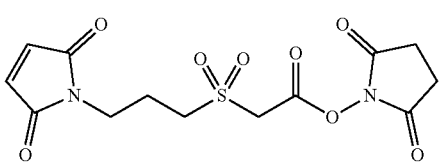

(Compound 25)

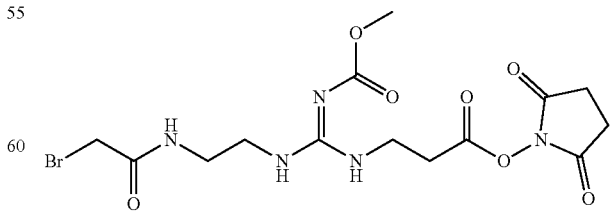

(Compound 26)

The above exemplary embodiments are used as illustrations of the invention. These embodiments are not intended to limit the scope of the invention. In fact, the invention is Scheme 1

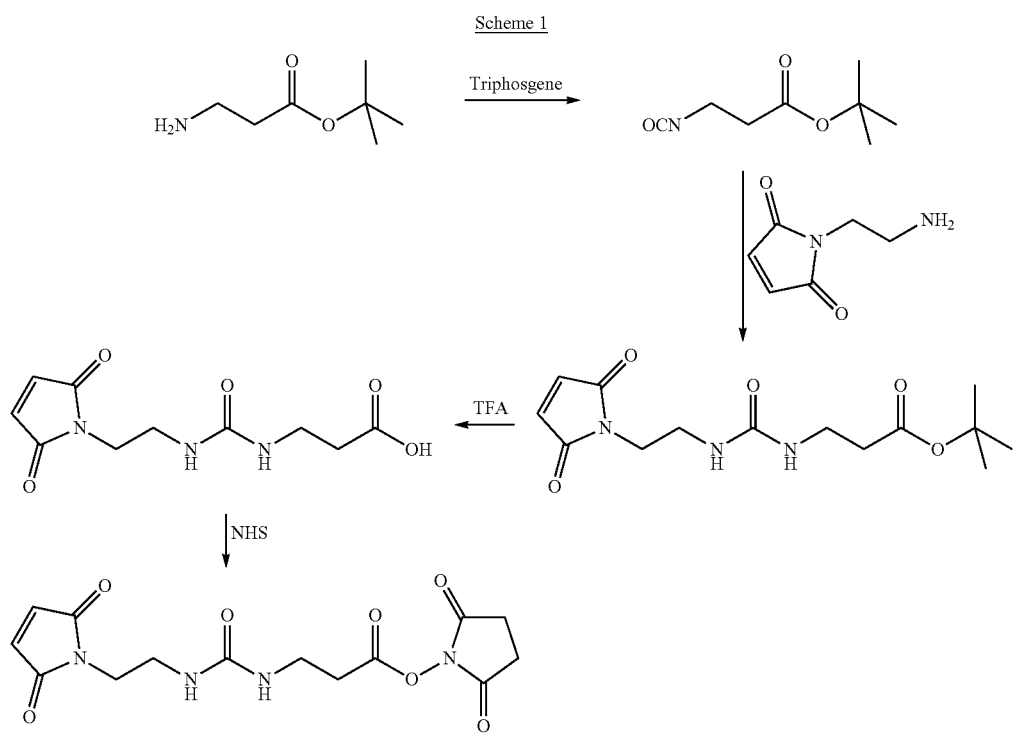

intended to cover all alternatives, modifications, and equivalents of these embodiments. It should not be understood that the present invention is only limited to the illustrated examples.

The Preparation of Hydrophilic Linkers Another aspect of the present invention is the preparation of hydrophilic linkers. The hydrophilic linkers of the invention can be prepared by many synthetic methods. As illustrative examples, the general synthetic routes to some of the hydrophilic linkers are shown in Scheme (1) to (11).

In Scheme (1), a hydrophilic linker that possesses a urea group is prepared. In the first step, an isocyanate group is introduced by treating an amino group with triphosgene. Next, upon Scheme 2

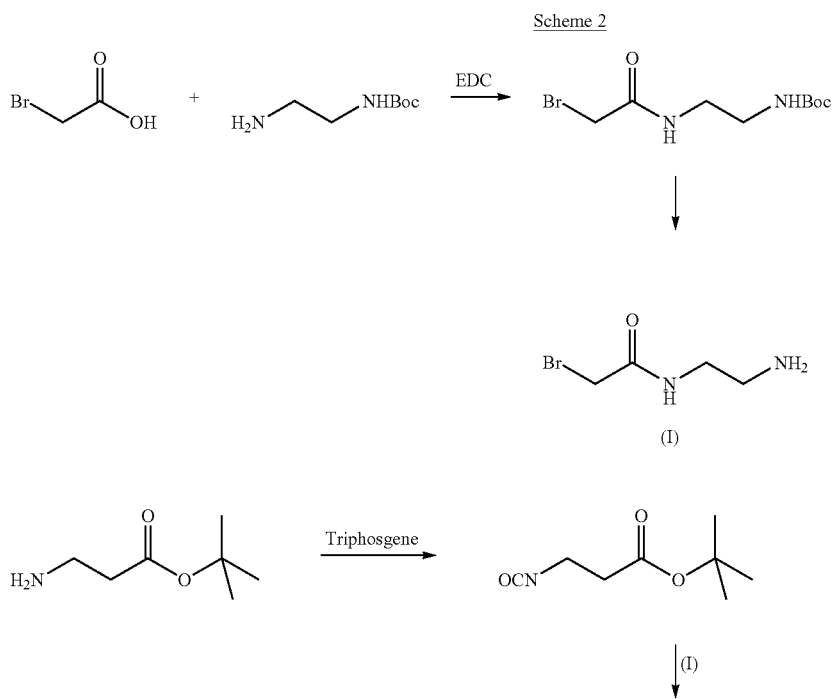

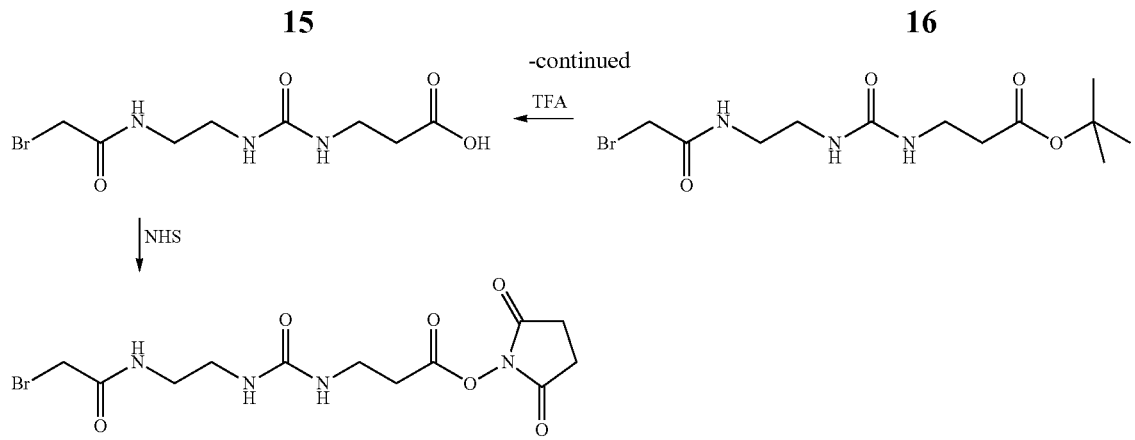

treatment with another amino group, a urea group easily forms in the middle of the hydrophilic linker. During the synthesis, a reactive maleimido group is introduced at the left terminus of the hydrophilic linkers at the same time. A reactive NHS group is introduced at the right terminus of the hydrophilic linker in the last step.

In Scheme (2), another hydrophilic linker that possesses a urea group is prepared. In the first step, a bromoacetamide derivative that possesses an amino group is prepared. Next, an isocyanate group is introduced by treating an amino group of a different compound with triphosgene. Then, upon reacting with the bromoacetamide derivative prepared in the first step, a urea group easily forms in the middle of the hydrophilic linker. During the synthesis, a reactive bromo group is introduced at the left terminus of the hydrophilic linkers at the same time. A reactive NHS group is introduced at the right terminus of the hydrophilic linker in the last step.

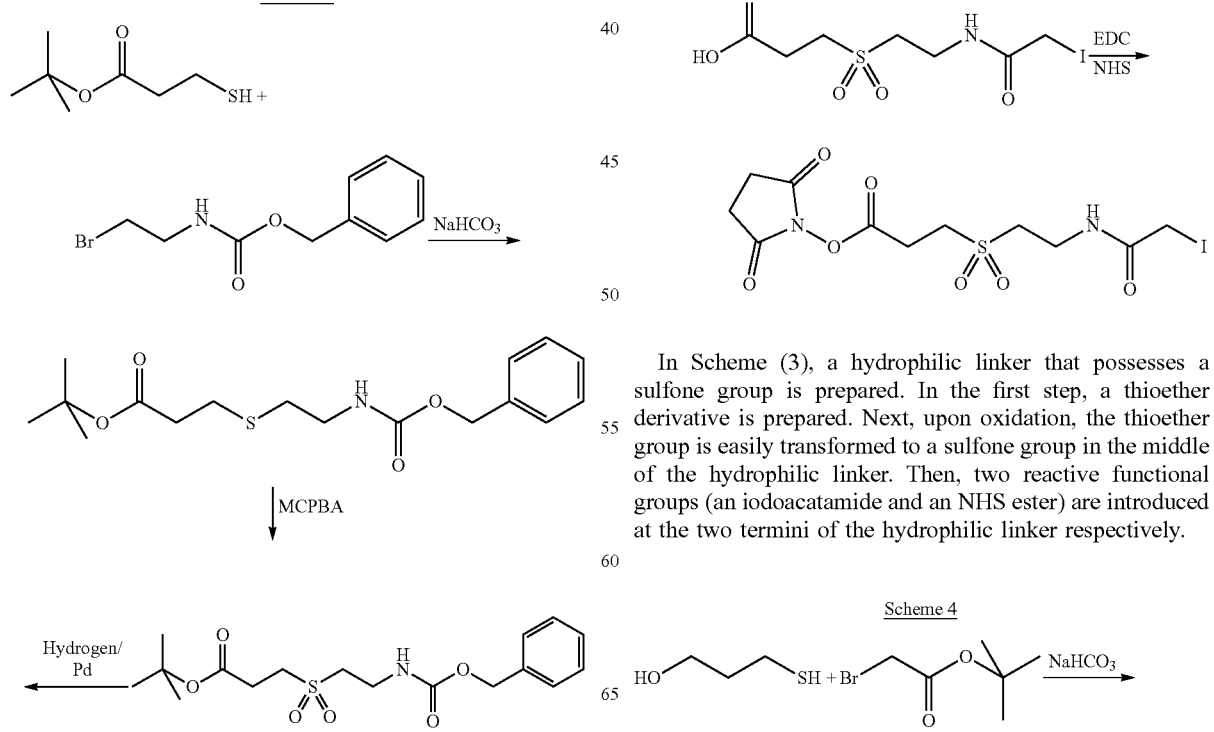

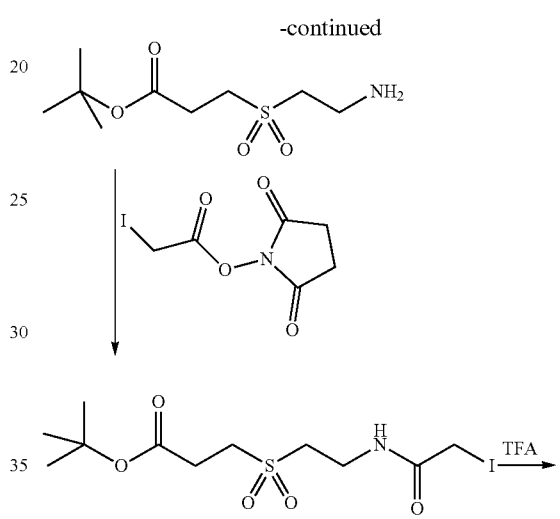

In Scheme (3), a hydrophilic linker that possesses a sulfone group is prepared. In the first step, a thioether derivative is prepared. Next, upon oxidation, the thioether group is easily transformed to a sulfone group in the middle of the hydrophilic linker. Then, two reactive functional groups (an iodoacatamide and an NHS ester) are introduced at the two termini of the hydrophilic linker respectively.

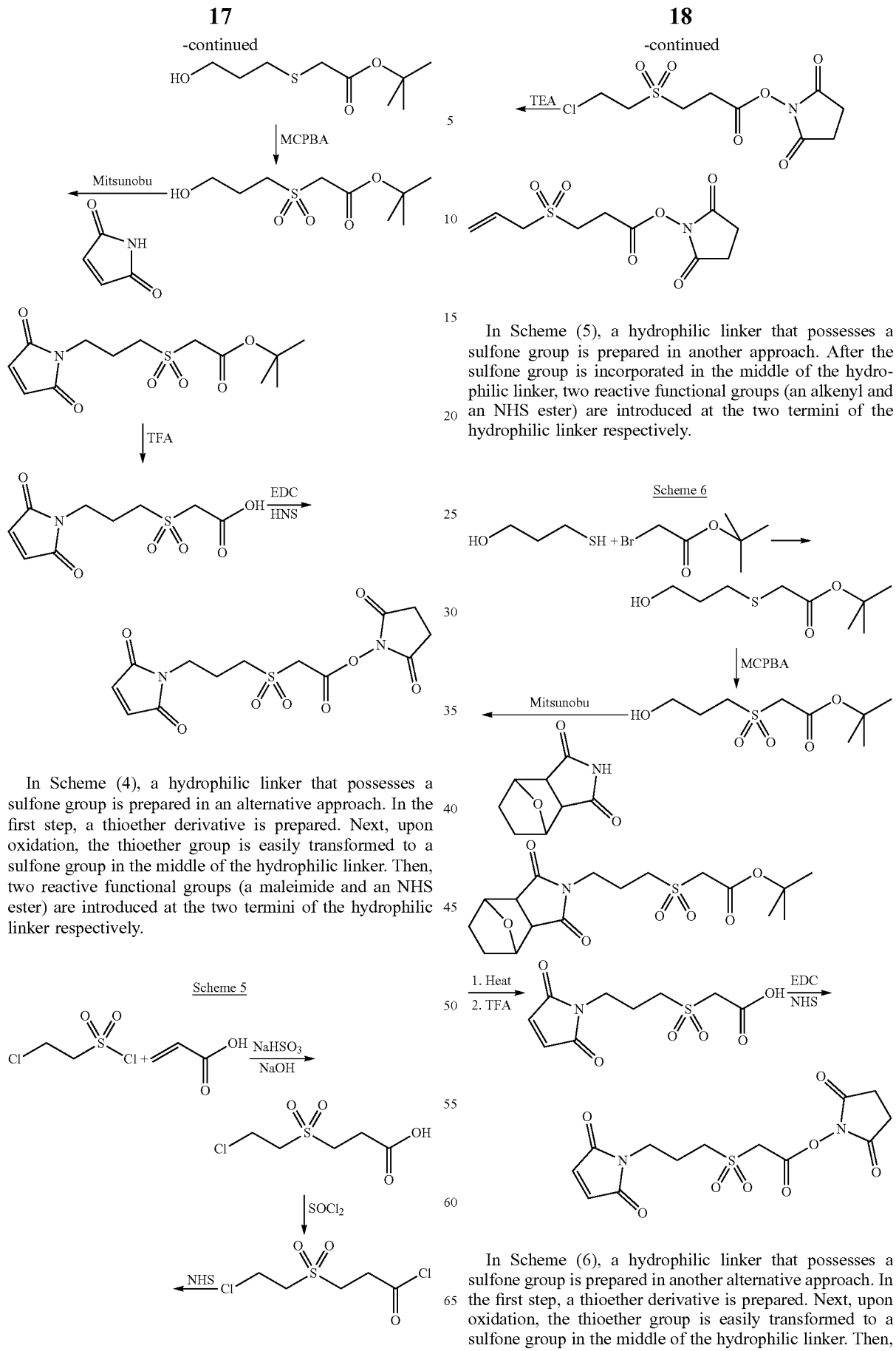

In Scheme (4), a hydrophilic linker that possesses a sulfone group is prepared in an alternative approach. In the first step, a thioether derivative is prepared. Next, upon oxidation, the thioether group is easily transformed to a sulfone group in the middle of the hydrophilic linker. Then, two reactive functional groups (a maleimide and an NHS ester) are introduced at the two termini of the hydrophilic linker respectively.

In Scheme (5), a hydrophilic linker that possesses a sulfone group is prepared in another approach. After the sulfone group is incorporated in the middle of the hydrophilic linker, two reactive functional groups (an alkenyl and an NHS ester) are introduced at the two termini of the hydrophilic linker respectively.

In Scheme (6), a hydrophilic linker that possesses a sulfone group is prepared in another alternative approach. In the first step, a thioether derivative is prepared. Next, upon oxidation, the thioether group is easily transformed to a sulfone group in the middle of the hydrophilic linker. Then, two reactive functional groups (a maleimide and an NHS ester) are introduced at the two termini of the hydrophilic linker respectively.

Scheme 7

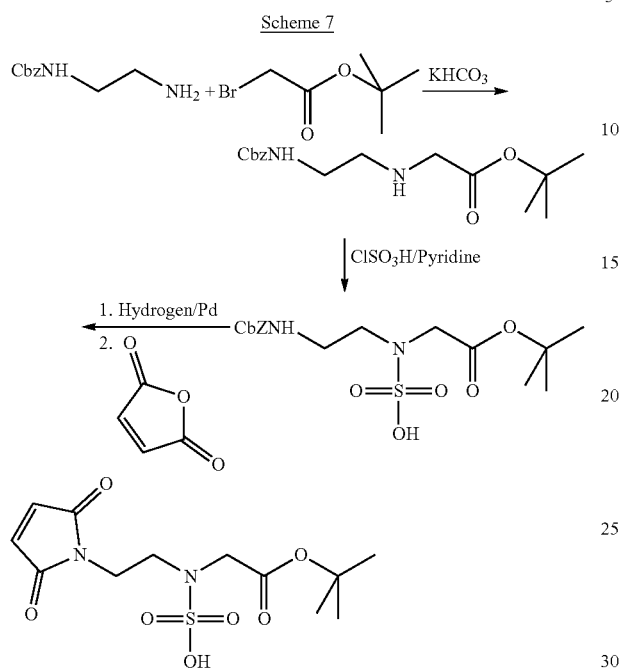

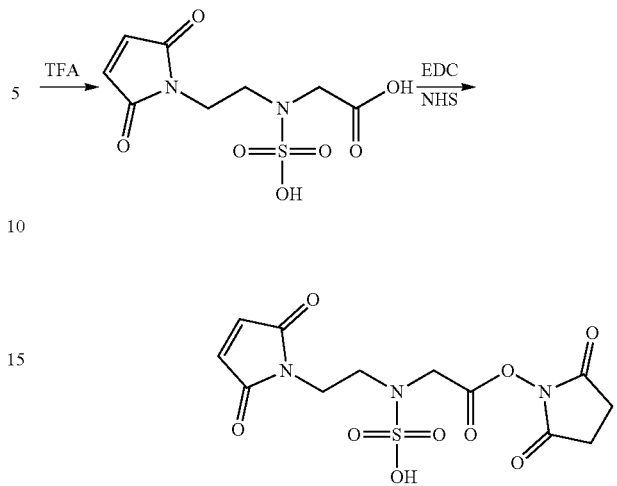

In Scheme (7), a hydrophilic linker that possesses a sulfamic acid group is prepared. In the first step, the needed amino group is created by a simple nucleophilic substitution reaction. Next, the sulfamic acid group is introduced in the middle of the hydrophilic linker by reacting with sulfurochloridic acid. Then, two reactive functional groups (a maleimide and an NHS ester) are introduced at the two termini of the hydrophilic linker respectively.

Scheme 8

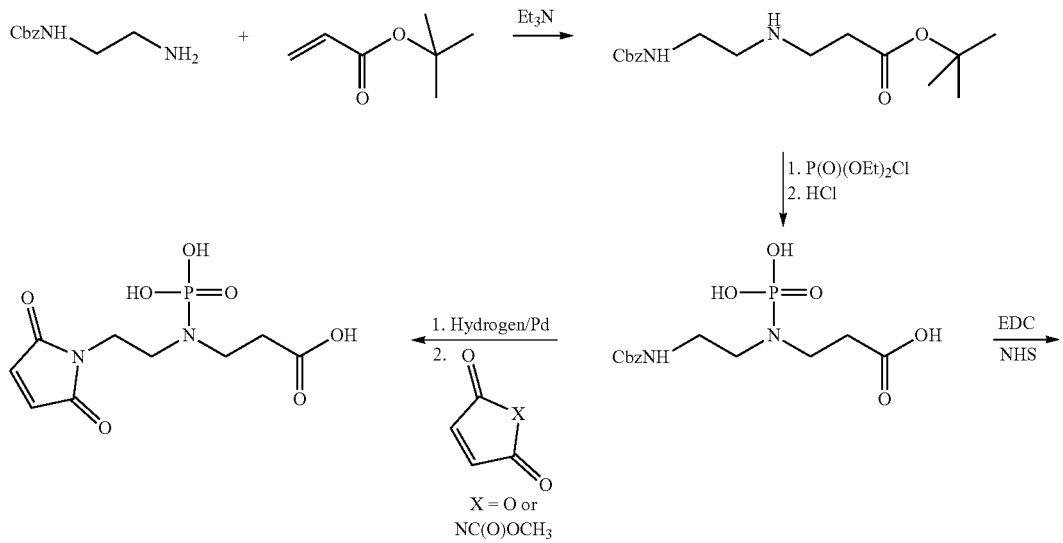

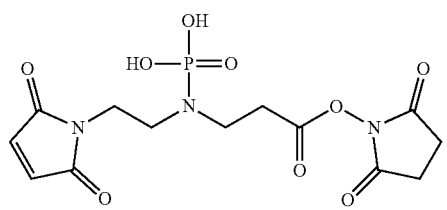

In Scheme (8), a hydrophilic linker that possesses a phosphoramidic acid group is prepared. In the first step, the needed amino group is created by a simple Michael addition reaction. Next, the phosphoramidic acid group is introduced in the middle of the hydrophilic linker by reacting with phosphoryl chloride or diethyl chlorophosphate, followed by treatment with hydrochloric acid. Then, two reactive functional groups (a maleimide and an NHS ester) are introduced at the two termini of the hydrophilic linker respectively.

In Scheme (9), a hydrophilic linker that possesses a sulfonamide group is prepared. In the first step, the needed amino group is created by a simple nucleophilic substitution reaction. Next, the sulfonamide group is introduced in the middle of the hydrophilic linker by reacting with mesyl chloride. Then, two reactive functional groups (a maleimide and an NHS ester) are introduced at the two termini of the hydrophilic linker respectively.

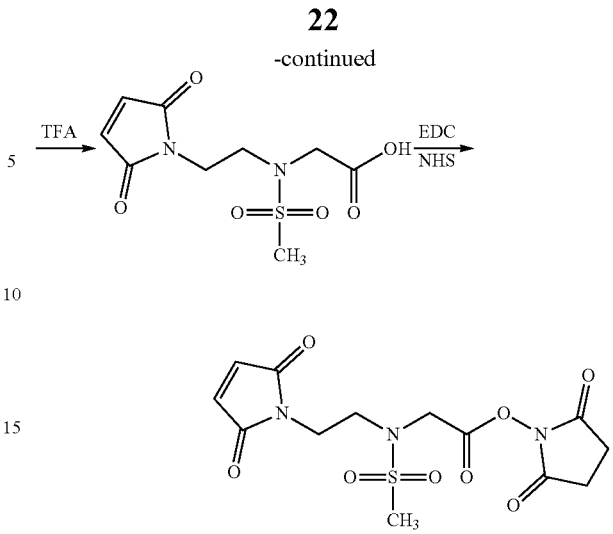

In Scheme (10), a hydrophilic linker that possesses a urea group is prepared. In the first step, the needed amino group is created by a simple nucleophilic substitution reaction. Next, the urea group is introduced in the middle of the hydrophilic linker by reacting with benzyl 4-nitrophenyl carbamate, which is prepared from benzylamine by reacting with 4-nitrophenyl chloroformate. Then, two reactive functional groups (a maleimide and an NHS ester) are introduced at the two termini of the hydrophilic linker respectively.

In Scheme (11), a hydrophilic linker that possesses a simple amino group is prepared. In the first step, the needed amino group is created by a simple nucleophilic substitution reaction, followed by reductive amination with formaldehyde or paraformaldehyde. Then, two reactive functional groups (a maleimide and an NHS ester) are introduced at the two termini of the hydrophilic linker respectively.

These exemplary embodiments are used as illustrations of the invention. These exemplary synthetic schemes are not intended to limit the synthetic methods of the hydrophilic linkers. The hydrophilic linkers of the present invention can also be prepared by various other approaches.

Scheme 9

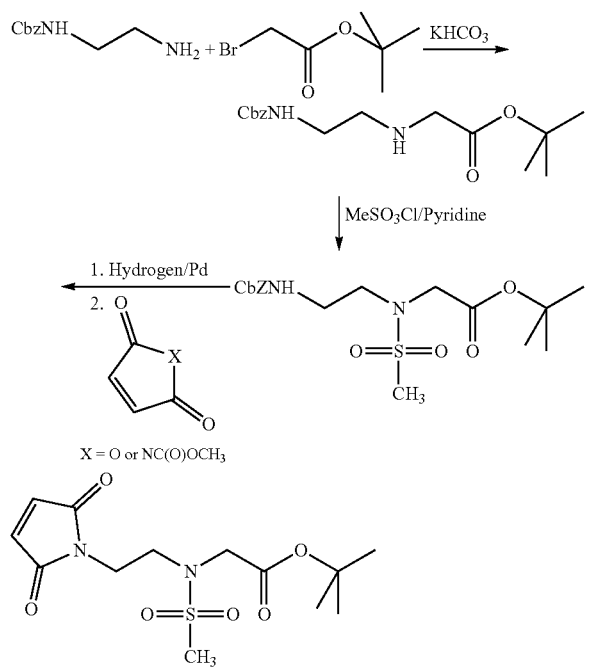

Scheme 10

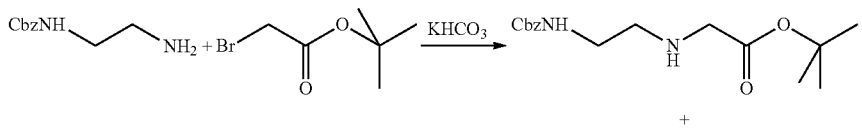

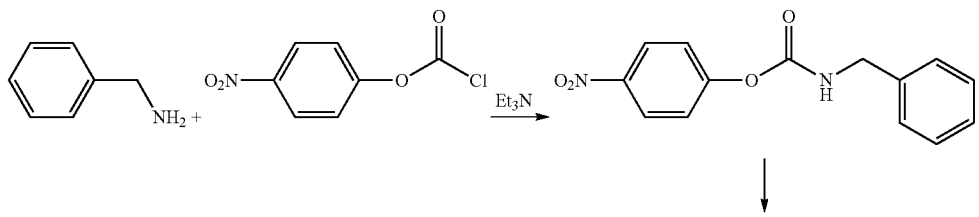

-continued

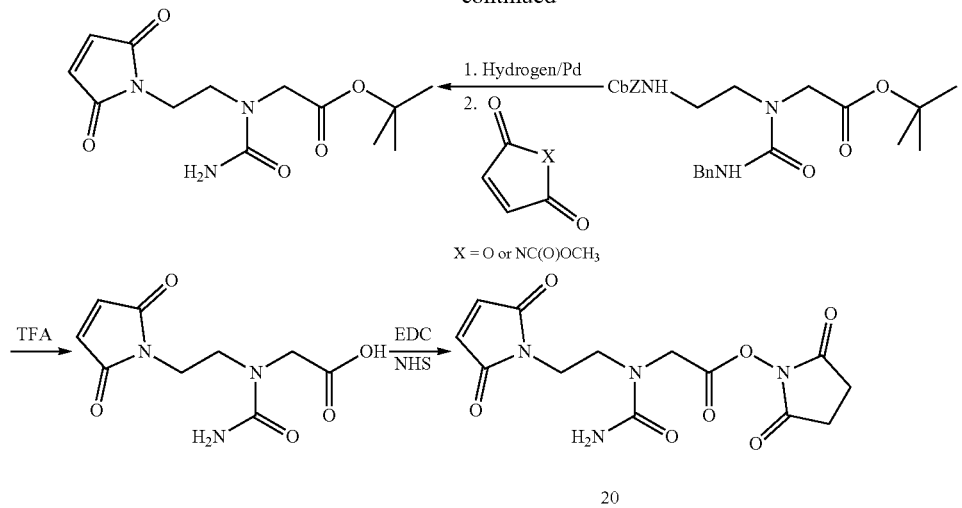

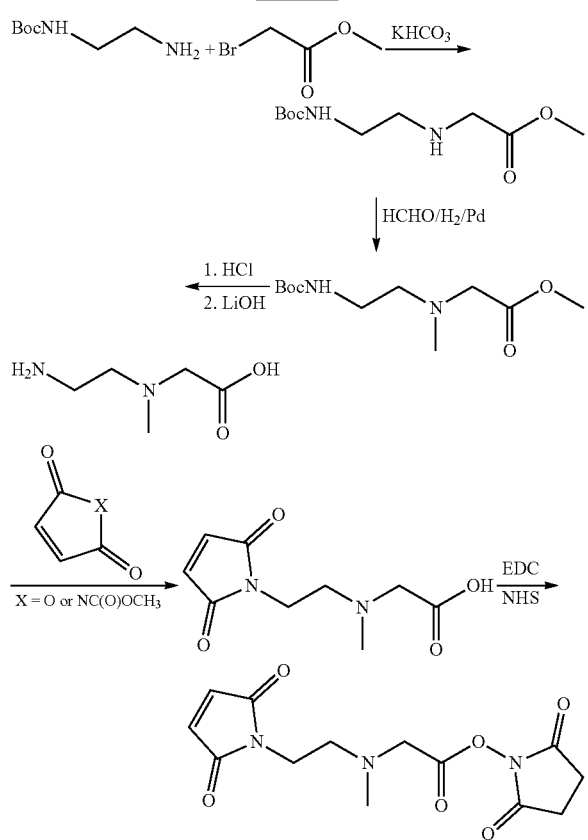

Ligand-Drug Conjugates

A further aspect of the present invention relates to novel ligand-drug conjugates. The present invention provides ligand-drug conjugates comprising a cell-binding ligand that binds to a particular cell population, a cytotoxic drug that is highly potent, and a hydrophilic linker that connects the cell-binding ligand and the cytotoxic drug. The ligand-drug conjugates of the present invention have superior efficacy and safety than ligand-drug conjugates comprising nonhydrophilic linkers.

The general formula of the antibody-drug conjugates of the present invention is shown in Formula (2):

$$D—U'—[X—V—Y]_n—W'—L \quad \text{Formula 2}$$

wherein:

D represents a cytotoxic drug;

L represents a cell-binding ligand;

V represents a polar or charged group; Suitable polar or charged groups that can be used in Formula (2) include, but are not limited to, aminos [—N(R)—], ureas [—N($R_1$)CON($R_2$)— or —N(CON$R_1R_2$)—], carboxyls [-Q(COOH)— or -Q(ZCOOH)—], carbamates {[—N(R)COO—] or [—N(COOR)—]}, guanidines [—N($R_1$)C=N(COO$R_2$)N($R_3$)—], sulfonamides [—N($SO_2$R)—], sulfones (—$SO_2$—), sulfoxides (—SO—), sulfonic acids [-Q(Z$SO_2$OH)—], sulfamic acids [—N($SO_2$OH)—], phosphonates {-Q[ZPO(OR)$_2$]—)}, phosphonic acids {-Q[ZPO(OH)$_2$]—}, phosphoramidic acids {—N[PO(OH)$_2$]—}, phosphorodiamidic acids {—N[PO(NH$_2$)(OH)]—}, and phosphoric triamides {—N[PO(NH$_2$)$_2$]—}, wherein R, $R_1$, $R_2$ and $R_3$ are independently H or $C_1$~$C_8$ alkyl; Q is CH or N; Z is 1~5 methylene units.

U' represents a functional group that enables a covalent linkage with a cytotoxic drug; The functional groups that enable a covalent linkage with a cytotoxic drug include, but are not limited to, thiols, disulfides, aminos, carboxyls, aldehydes, ketones, maleimides, haloacetyl groups, alkenyl groups, alkynyl groups, hydrazines, and hydroxyls. The covalent linkage with the cytotoxic drug can be a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, or a carbonate linkage;

W' represents a functional group that enables a covalent linkage with a cell-binding ligand, such as a monoclonal antibody. The functional groups that enable a covalent linkage with a cell-binding ligand mainly include two types. The first type of functional groups enable a covalent linkage with an amino group on the cell-binding ligand. These functional groups include, but are not limited to, N-hydroxysuccinimide esters, N-sulfosuccinimidyl esters, nitrophenyl esters, dinitrophenyl esters, pentafluorophenyl esters, tetrafluorophenyl esters, acyl chlorides, anhydrides, sulfonyl chlorides, chloroformates, isocyanates, isothiocyanates, aldehydes, and ketones. The covalent linkage can be an amide linkage, a carbamate linkage, a urea linkage, or other types of carbon-nitrogen bonds. The second type of functional groups enable a covalent linkage with a thiol group on the cell-binding ligand. These functional groups include, but are not limited to, disulfides such as pyridyldisulfides and nitropyridyldisulfides, maleimides, acyl chlorides, haloacetyl groups such as iodoacetamide and bromoacetamide, alkenyl pyridines, isocyanates, and isothiocyanates. The covalent linkage can be a disulfide linkage, a thioether linkage, a thiocarbamate linkage, a dithiocarbamate linkage, or a thioester linkage;

X represents a component composed of one, two, or three methylene units. The methylene units can be optionally substituted with alkyl, halo, hydroxyl, or alkoxy groups;

Y represents a component composed of one, two, or three methylene units. The methylene units can be optionally substituted with alkyl, halo, hydroxyl, or alkoxy groups;

n is an integer from 1 to 100. If n>1, the values of each V, X, and Y in the repeating brackets of Formula (2) are independent and do not have to be identical.

Preferably n is an integer from 1 to 50. Even more preferably, n is an integer from 1 to 10. Most preferably n is an integer from 1 to 4.

The Cytotoxic Drug

The drug moiety in the ligand-drug conjugate of the present invention is a potent cytotoxic agent for the purpose of cancer therapy. The cytotoxic drugs include alkylating agents, anti-metabolites, anti-microtubule agents, topoisomerase inhibitors, cytotoxic antibiotics, DNA intercalators and any other molecule that is highly cytotoxic and can therefore lead to cell death. Exemplary types of the cytotoxic drugs include the nitrogen mustards, the anthracyclines, the vinca alkaloids, the mitomycins, the bleomycins, the nucleoside analogues, the pteridines, the diynenes (also called enediynes, bicyclodiynenes or bicyclic enediynes), the podophyllotoxins, dolastatins (including auristatins), maytansinoids, tubulysins, pyrrolo[2,1-c][1,4]benzodiazepines (PBD), and taxanes. Exemplary members of these types of cytotoxic drugs include mechlorethamine, cyclophosphamide, melphalan, chlorambucil, ifosfamide, busulfan, carmustine (BCNU), lomustine (CCNU), semustine (MeCCNU), fotemustine, streptozotocin, dacarbazine, mitozolomide, temozolomide, thiotepa, mytomycin, diaziquone (AZQ), cisplatin, carboplatin, oxaliplatin, procarbazine, hexamethylmelamine, nedaplatin, satraplatin, triplatin tetranitrate, bendamustine, uramustine, purine analogues, pyrimidine analogues, nucleoside analogues, nucleotide analogues, methotrexate, pemetrexed, raltitrexed, fluorouracil, capecitabine, cytarabine, gemcitabine, decitabine, 5-azacytidine, fludarabine, nelarabine, cladribine, clofarabine, pentostatin, thioguanine, vincristine, vinblastine, vinorelbine, vindesine, vinflunine, paclitaxel, docetaxel, dolastatin A, dolastatin B, dolastatin 10, dolastatin 13, dolastatin 14, dolastatin 15, dolastatin 16, dolastatin 17, dolastatin 18, auristatin E, auristatin EB (AEB), auristatin EFP (AEFP), monomethyl auristatin E (MMAE), monomethyl auristatin F (MMAF), DM1, DM3, DM4, tubulysins, duocarmycins, epothilones, podophyllotoxin, etoposide, etoposide phosphate, teniposide, irinotecan, topotecan, etoposide, mitoxantrone, teniposide, merbarone, aclarubicin, novobiocin, plicamycin, lamellarin, ellipticine, amsacrine, aurintricarboxylic acid, bleomycin, mitomycin A, mitomycin C, daunorubicin, doxorubicin, epirubicin, idarubicin, pirarubicin, aclarubicin, mitoxantrone, actinomycin, dactinomycin, cytosine arabinoside, methopterin, dichloromethotrexate, leurosine, leurosideine, caminomycin, aminopterin, tallysomycini, podophyllotoxin, butyric acid, camptothecin, calicheamicin, esperamicin, dynemicin, neocarzinostatin (NCS), kedarcidin, C1027, and their analogues.

The average number of the drug units in each antibody-drug conjugate molecule is from 1 to 8, preferably from 2 to 6.

Depending on the synthetic need of the ligand-drug conjugate, it may be necessary to modify the structure of the drug moiety in order to make it more fasible or more convenient to prepare the ligand-drug conjugate. For example a reactive functional group, such as amino, hydroxyl, thiol, or carboxyl group, may be introduced to the drug structure at a suitable position. Of course, such modification should have minimal harmful effect on the potency and other properties of the parent drug.

Some drugs already possess suitable functional groups that can be used to couple to the hydrophilic linker for the preparation of ligand-drug conjugates. For examples, the following drugs possess an inherent amino group for such linkage: mitomycins, dolastatins (including auristatins), daunorubicin, doxorubicin, aminopterin, bleomycin, actinomycin, tallysomycin, 9-amino camptothecin, and cytarabine. Likewise, the following drugs possess an inherent hydroxyl group that can be used to couple to the hydrophilic linker for the preparation of ligand-drug conjugates: paclitaxel, etoposide, podophyllotoxin, camptothecin, esperamicin, vinblastine, vincristine, and doxorubicin; and the following drugs possess an inherent thiol group or a functional group that can be easily transformed to a thiol group for the preparation of ligand-drug conjugates: esperamicin, calicheamicin, esperamicin, and 6-mercaptopurine.

Preferably, the in vitro potency of the cytotoxic drugs for use in ligand-drug conjugates of the present invention are higher than that of traditional chemotherapeutic drugs. The cytotoxic drugs are preferably stable and adequately soluble in aqueous milieu.

More preferably, the cytotoxic drugs for use in the ligand-drug conjugates of the present invention are maytansinoids, dolastatins (in particular auristatins), calicheamicins, tubulysins, mitomycins, vinca alkaloids, anthracyclines, duocarmycins, and pyrrolo[2,1-c][1,4]benzodiazepines (PBD). These cytotoxic drugs possess high potency for use in ligand-drug conjugates such as antibody-drug conjugates of the present invention.

Maytansinoids:

Maytansine was first isolated from the bark of the Ethiopian shrub *Maytenus ovatus* and is 100-1000 times more cytotoxic than conventional chemotherapeutic drugs. Maytansine and maytansinoids bind tightly to tubulin and potently inhibit microtubule dynamics during mitosis. The strong inhibition ultimately leads to cell death by apoptosis.

Preferred maytansinoids are shown in Formula (3), wherein $R_1$ and $R_2$ are independently H or $C_1$~$C_8$ alkyl, m is 1, 2, or 3. The thiol group is used for covalent coupling to the hydrophilic linker, which in turn connects to a cell-binding ligand, such as an antibody, in the ligand-drug conjugates of the present invention. More preferred maytansinoids include DM1, DM3 and DM4.

When maytansinoids are used as the cytotoxic drugs for the ligand-drug conjugates of the present invention, the hydrophilic linkers in the ligand-drug conjugates, such as antibody-drug conjugates, are preferably non-cleavable. After binding to the antigen on the surface of tumor cells and internalized by endocytosis, the antibody portion of the antibody-drug conjugate is proteolytically degraded in lysosome until only a single amino acid residue remains connected to the hydrophilic linker. The amino acid that remains connected to the hydrophilic linker is the amino acid that is used as the anchor of the antibody to connect to the hydrophilic linker. The most convenient amino acids to anchor the linkage are lysine and cysteine. The amino acid-linker-maytansinoid catabolite, such as lysine-linker-maytansinoid catabolite or cysteine-linker-maytansinoid catabolite, produced via proteolytical degradation binds to tubulin in the cytoplasm and induces apoptosis. The amino acid-linker-maytansinoid catabolite is also highly resistant to MDR1, because the hydrophilic linker and the attached amino acid will render the entire catabolite highly hydrophilic.

Formula 3

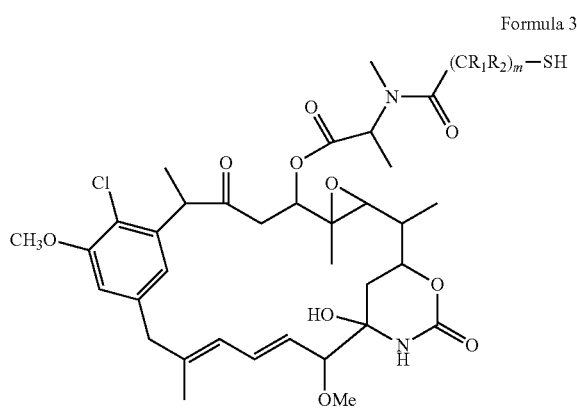

Dolastatins:

The dolastatins were first discovered in the sea hare *Dolabella auricularia*. Dolastatins and their peptidic analogs are highly potent antimitotic agents that inhibit tubulin-dependent GTP binding and microtubule dynamics. Their high potency makes dolastatins including auristatins highly effective drugs for the ligand-drug conjugates of the present invention.

Preferred dolastatins for the ligand-drug conjugates of the present invention include monomethyl auristatin E (MMAE) and monomethyl auristatin F (MMAF). Both MMAE and MMAF can be attached to the hydrophilic linker via either the N (amino) terminus or the C (carboxyl) terminus of the peptidic drug.

When MMAF is used as the cytotoxic drug for the ligand-drug conjugates of the present invention, the hydrophilic linker in the ligand-drug conjugates, such as antibody-drug conjugates, is preferably non-cleavable. After being internalized into tumor cells, the antibody portion of the ADC is proteolytically degraded to give a catabolite that contains MMAF, the hydrophilic linker, and a residual amino acid of the antibody. The amino acid that remains connected to the hydrophilic linker is the amino acid that is used as the anchor of the antibody to connect to the hydrophilic linker. For example, if cysteine is used as the anchoring amino acid, the three-component catabolite will be cysteine-linker-MMAF. The three-component catabolite binds to tubulin in the cytoplasm to disrupt microtubule dynamics and induce apoptosis. The catabolite is also highly resistant to MDR1, because the hydrophilic linker and the attached amino acid will render the entire catabolite highly hydrophilic.

The Cell-Binding Ligand

The ligand moiety in the ligand-drug conjugate of the present invention is a cell-binding molecule that selectively binds to target cancer cells. The cell-binding ligands include any molecular agent that specifically binds to receptors or other antigens on the target cells. The cell-binding ligand is coupled to the linker moiety of the ligand-drug conjugate via the use of an inherent or artificially introduced functional group, such as thiol, amino, aldehyde or carboxyl groups. The cell-binding ligand acts to deliver the linked cytotoxic drugs to the tumor cells. After binding to the target cells, the ligand-drug conjugates are internalized first. Following its fragmentation inside the cells, the cytotoxic drugs are released to the cytoplasm to kill the tumor cells. The cell-binding ligand can be any protein or protein-like molecule that binds to, complexes with, or reacts with a receptor or antigen on the target cell. Both immunoglobulin and non-immunoglobulin proteins that bind specifically to target receptors or antigens on the cancer cells are acceptable. For example, full-length antibodies, antibody fragments, antibody mimetics, polypeptides, peptide ligands, and non-peptide ligands can all be used for the ligand-drug conjugates of the present invention.

Specifically, the cell-binding ligands include the following molecular agents:

(1). Resurfaced, chimeric, humanized and fully human antibodies: Antibodies, polyclonal and in particular monoclonal, are excellent cell-binding ligands for the ligand-drug conjugates of the present invention. The resurfaced, chimeric, humanized and fully human antibodies are more preferred because they are less likely to cause immunogenicity in humans.

The antibody for the antibody-drug conjugate of the present invention may also be a bifunctional antibody that has one arm having a specificity for one antigenic site, while the other arm recognizes a different target. Alternatively, each arm of the bifunctional antibody may have specificity for a different epitope of the same tumor associated antigen of the cell. The dual specificity allows the antibody-drug conjugates to possess more benefits for therapeutic treatment.

Specific antibodies that can be used for the antibody-drug conjugates of the present invention include, but are not limited to, anti-HER2 monoclonal antibody such as trastuzumab and pertuzumab, anti-CD20 monoclonal antibody such as rituximab, ofatumumab, tositumomab and ibritumomab, anti-CA125 monoclonal antibody such as oregovomab, anti-EpCAM (17-1A) monoclonal antibody such as edrecolomab, anti-EGFR monoclonal antibody such as cetuximab, panitumumab and nimotuzumab, anti-CD30 monoclonal antibody such brentuximab, anti-CD33 monoclonal antibody such as gemtuzumab and huMy9-6, anti-vascular integrin alpha-v beta-3 monoclonal antibody such as etaracizumab, anti-CD52 monoclonal antibody such as alemtuzumab, anti-CD22 monoclonal antibody such as epratuzumab, anti-CEA monoclonal antibody such as labetuzumab, anti-CD44v6 monoclonal antibody such as bivatuzumab, anti-FAP monoclonal antibody such as sibrotuzumab, anti-CD19 monoclonal antibody such as huB4, anti-CanAg monoclonal antibody such as huC242, anti-CD56 monoclonal antibody such huN901, anti-CD38 monoclonal antibody such as daratumumab, anti-CA6 monoclonal antibody such as DS6, anti-IGF-IR monoclonal antibody such as cixutumumab and 3B7, anti-integrin monoclonal antibody such as CNTO 95, and anti-syndecan-1 monoclonal antibody such as B-B4.

(2). Antigen-binding fragments of antibodies: Use of antigen-binding fragments of antibodies, instead of whole antibodies, offers the advantage of greater tumor penetration because of their smaller size. In addition, the antigen-binding fragments of antibodies are more evenly distributed throughout the tumor mass as compared to whole antibodies.

The antigen-binding fragments that can be used for the ligand-drug conjugates of the present invention include, but are not limited to, single-chain variable fragment (sFv or scFv), single-domain antibody (sdAb), Fab fragment, Fab' fragment, F(ab')2 fragment, and other types of antigen recognizing immunoglobulin fragments. The immunoglobulin fragments can be prepared by various methods known in the art, for example, by digestion with proteolytic enzymes such as pepsin or papain, reductive alkylation, or recombinant techniques.

(3). Non-immunoreactive proteins and polypeptides: Other than antibodies and antibody fragments, any other ligand that binds to a cell receptor or surface antigen can also be used as the cell-binding ligand for the ligand-drug conjugates of the present invention. These ligands include, but are not limited to, interferons such as IFN-α, IFN-β, and IFN-γ, transferrins, epidermal growth factors (EGF) and EGF-like domains, gastrin-releasing peptides (GRP), platelet-derived growth factors (PDGF), transforming growth factors (TGF), vaccinia growth factor (VGF), insulin and insulin-like growth factors (IGF) such as IGF-1 and IGF-2, other suitable hormones such as thyrotropin releasing hormones (TRH), melanocyte-stimulating hormones (MSH), steroid hormones (for example, estrogen and androgen), and somatostatin, lymphokines such as IL-2, IL-3, IL-4, and IL-6, colony-stimulating factors (CSF) such as G-CSF, M-CSF and GM-CSF, bombesin, gastrin, and folic acid.

One of the key factors that determine the outcome of a ligand-drug conjugate is the cell receptor or surface antigen that is selected as the target for the cell-binding ligand. The cell receptors and surface antigens that the cell-binding ligands bind to include, but are not limited to, tumor associated antigens such as HER2, HER3 and HER4, epidermal growth factor receptors (EGFR), astrin-releasing peptide receptor (GRPR), bone morphogenetic protein receptor I B (BMPR1B), folate receptor, metalloreductase STEAP1, sodium-dependent phosphate transport protein 2B (Napi3b or SLC34A2), brevican, ephrin receptors (Ephs) such as EphB2R and EphA receptors, prostate stem cell antigen (PSCA), B cell activating factor of the TNF family receptor (BAFF-R), C-X-C chemokine receptor type 5 (CXC-R5, CD185, or BLR1), HLA class II histocompatibility antigen-DO beta chain (HLA-DOB), P2X purinoceptor 5 (P2X5 or P2RX5), transferrin receptors (TfR), hormone receptors, growth-hormone-releasing hormone receptor (GHRHR), epithelial cell adhesion molecule such as LFA-1, Mac 1, VLA-4, ICAM-1, VCAM, and EpCAM, gangliosides such as GD3, FMS-like tyrosine kinase 3 (FLT3), prostate-specific membrane antigen (PSMA), mucin 1 (MUC1), mucin 16 (MUC16 or CA-125), six transmembrane epithelial antigen of prostate (STEAP), carcinoembryonic antigen (CEA), decay accelerating factor (DAF or CD55), folate receptors such as folate receptor 1 (FOLR1), mesothelin, cryptic family protein 1B (Cripto), integrins such as alphavbeta6 and alpha4beta1 (VLA-4), growth factors such as VEGF, VEGF receptors (VEGFR), transferrins receptors, transport proteins, homing receptors, endothelial cell-linked antigens such as endoglin, IGF-IR, CanAg, and C242 antigens, and many CD molecules such as CD2, CD3, CD4, CD5, CD6, CD8, CD11a, CD11b, CD11c, CD14, CD18, CD19, CD20, CD21, CD22, CD23, CD25, CD26, CD28, CD30, CD33, CD36, CD37, CD38, CD40, CD44, CD52, CD56, CD59, CD70, CD72, CD79a, CD79b, CD80, CD81, CD103, CD105, CD134, CD137, CD138, and CD152.

Preferred cell-binding ligands of the present invention are monoclonal antibodies. The resurfaced, chimeric, humanized and fully human antibodies are more preferred because they are less likely to cause immunogenicity in humans.

Preferred antibody-drug conjugates of the present invention are shown in Formulas (4) and (5):

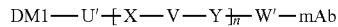

Formula 4

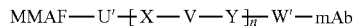

Formula 5 wherein:

DM1 represents maytansinoid DM1;

MMAF represents monomethyl auristatin F;

mAb represents a cell-binding monoclonal antibody; V represents a polar or charged group; Suitable polar or charged groups that can be used in Formulas (4) and (5) include, but are not limited to, aminos [—N(R)—], ureas [—N(R$_1$)CON(R$_2$)— or —N(CONR$_1$R$_2$)—], carboxyls [-Q (COOH)— or -Q(ZCOOH)—], carbamates {[—N(R)COO—] or [—N(COOR)—]}, guanidines [—N(R$_1$)C=N(COOR$_2$)N(R$_3$)—], sulfonamides [—N(SO$_2$R)—], sulfones (—SO$_2$—), sulfoxides (—SO—), sulfonic acids [-Q(ZSO$_2$OH)—], sulfamic acids [—N(SO$_2$OH)—], phosphonates {-Q[ZPO(OR)$_2$]—}, phosphonic acids {-Q[ZPO(OH)$_2$]—}, phosphoramidic acids {—N[PO(OH)$_2$]—}, phosphorodiamidic acids {—N[PO(NH$_2$)(OH)]—}, and phosphoric triamides {—N[PO(NH$_2$)$_2$]—}, wherein R, R$_1$, R$_2$ and R$_3$ are independently H or C$_1$~C$_8$ alkyl; Q is CH or N; Z is 1~5 methylene units.

U' represents a functional group that enables a covalent linkage with the cytotoxic drug; The functional groups that enable a covalent linkage with the cytotoxic drug include, but are not limited to, thiols, disulfides, aminos, carboxyls, aldehydes, ketones, maleimides, haloacetyl groups, alkenyl groups, alkynyl groups, hydrazines, and hydroxyls. The covalent linkage with the cytotoxic drug can be a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, or a carbonate linkage;

W' represents a functional group that enables a covalent linkage with a cell-binding ligand, such as a monoclonal antibody. The functional groups that enable a covalent linkage with a cell-binding ligand mainly include two types. The first type of functional groups enable a covalent linkage with an amino group on the cell-binding ligand. These functional groups include, but are not limited to, N-hydroxysuccinimide esters, N-sulfosuccinimidyl esters, nitrophenyl esters, dinitrophenyl esters, pentafluorophenyl esters, tetrafluorophenyl esters, acyl chlorides, anhydrides, sulfonyl chlorides, chloroformates, isocyanates, isothiocyanates, aldehydes, and ketones. The covalent linkage can be an amide linkage, a carbamate linkage, a urea linkage, or other types of carbon-nitrogen bonds. The second type of functional groups enable a covalent linkage with a thiol group on the cell-binding ligand. These functional groups include, but are not limited to, disulfides such as pyridyldisulfides and nitropyridyldisulfides, maleimides, acyl chlorides, haloacetyl groups such as iodoacetamide and bromoacetamide, alkenyl pyridines, isocyanates, and isothiocyanates. The covalent linkage can be a disulfide linkage, a thioether linkage, a thiocarbamate linkage, a dithiocarbamate linkage, or a thioester linkage;

X represents a component composed of one, two, or three methylene units. The methylene units can be optionally substituted with alkyl, halo, hydroxyl, or alkoxy groups;

Y represents a component composed of one, two, or three methylene units. The methylene units can be optionally substituted with alkyl, halo, hydroxyl, or alkoxy groups;

n is an integer from 1 to 100. If n>1, the values of each V, X, and Y in the repeating brackets of Formulas (4) and (5) are independent and do not have to be identical.

Preferably n is an integer from 1 to 50. Even more preferably, n is an integer from 1 to 10. Most preferably n is an integer from 1 to 4.

As exemplary embodiments of the invention, some of the antibody-drug conjugates of the present invention are shown in the structures below [Compound (27) to (98)]:

(Compound 27)
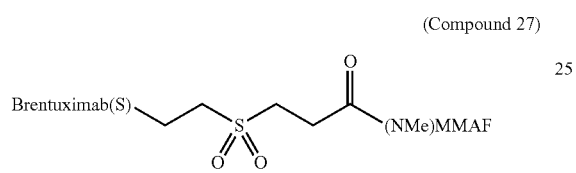

(Compound 28)
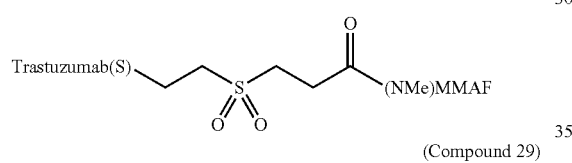

(Compound 29)
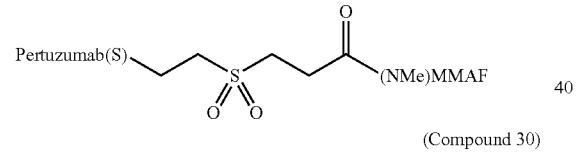

(Compound 30)
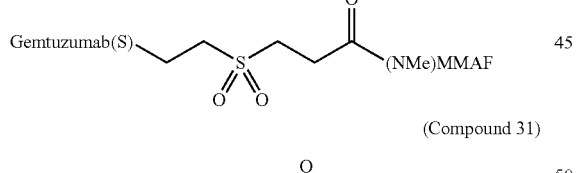

(Compound 31)
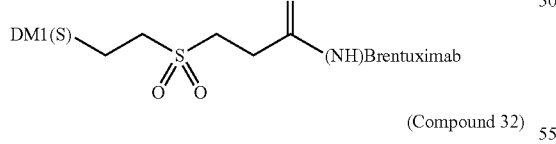

(Compound 32)
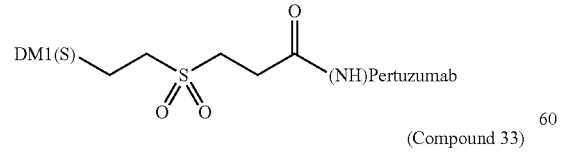

(Compound 33)
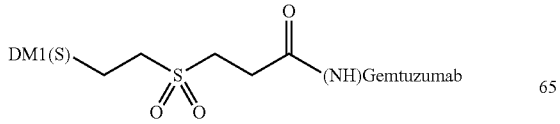

(Compound 34)
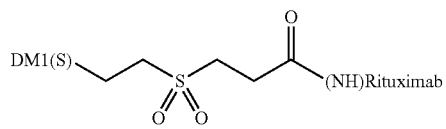

(Compound 35)
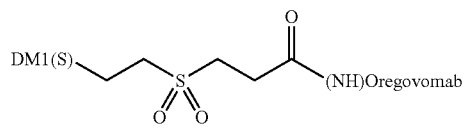

(Compound 36)
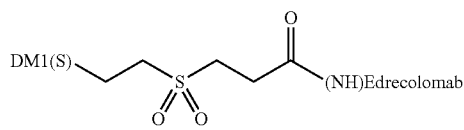

(Compound 37)
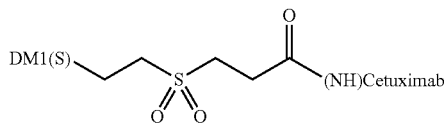

(Compound 38)
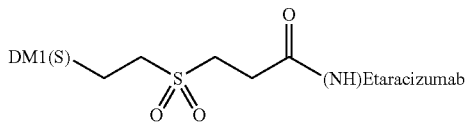

(Compound 39)
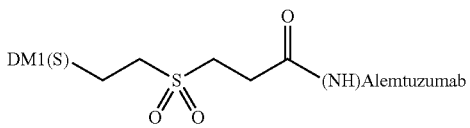

(Compound 40)
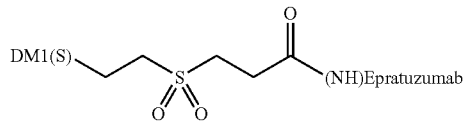

(Compound 41)
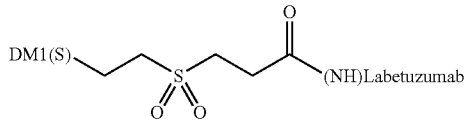

(Compound 42)
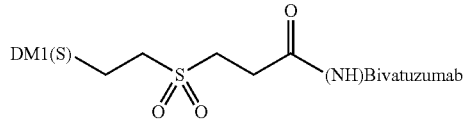

(Compound 43)
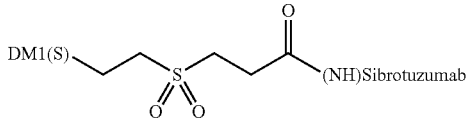

(Compound 44)
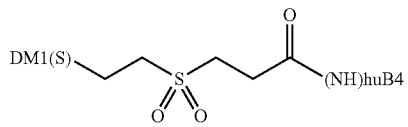
(Compound 45)
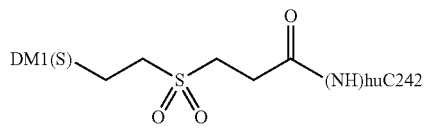
(Compound 46)
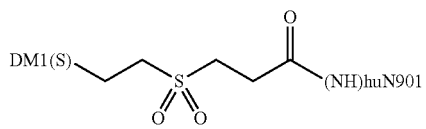
(Compound 47)
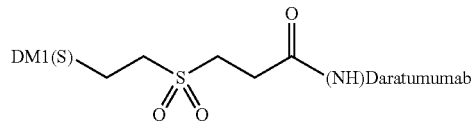
(Compound 48)
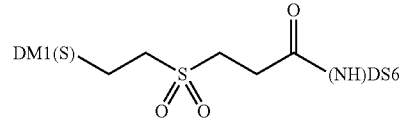
(Compound 49)
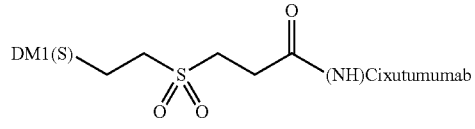
(Compound 50)
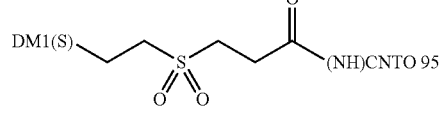
(Compound 51)
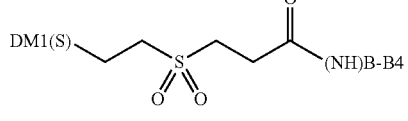
(Compound 52)
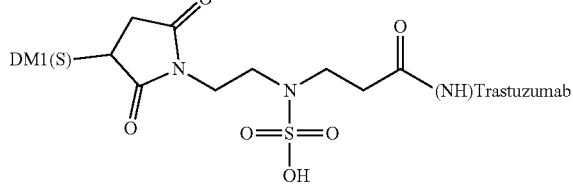
(Compound 53)
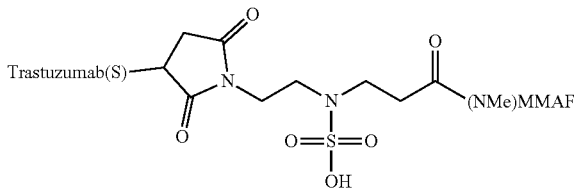
(Compound 54)
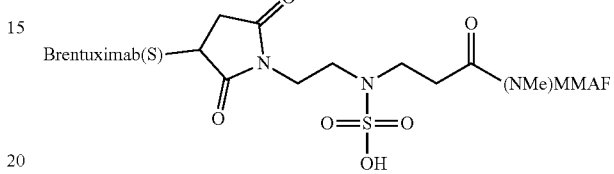
(Compound 55)
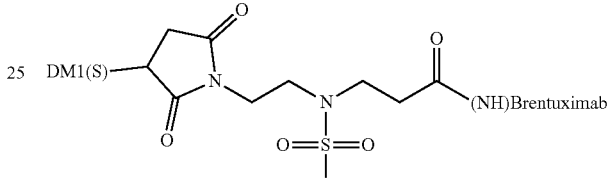
(Compound 56)
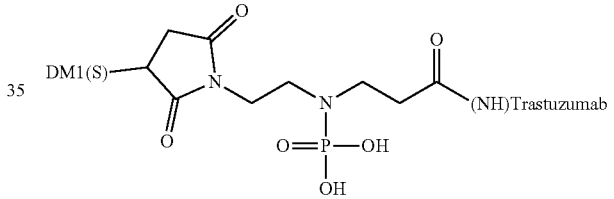
(Compound 57)
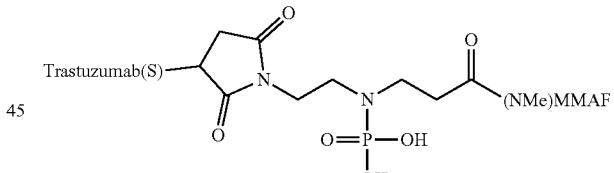
(Compound 58)
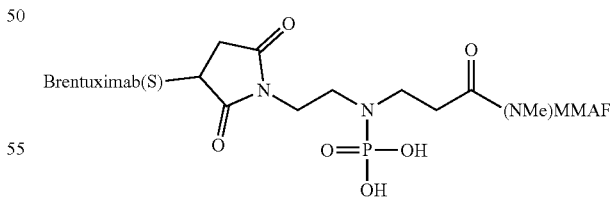
(Compound 59)
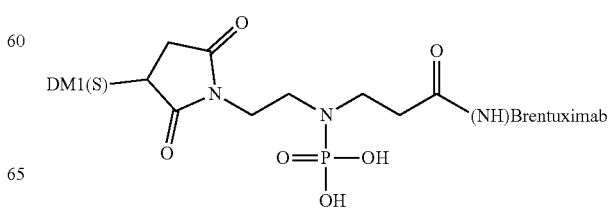

(Compound 60)
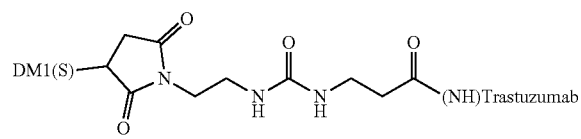
(Compound 61)
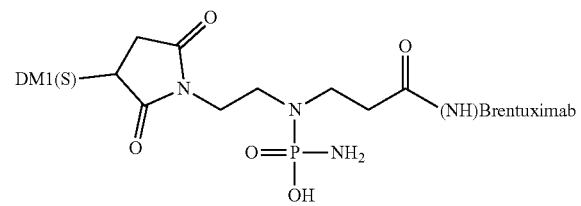
(Compound 62)
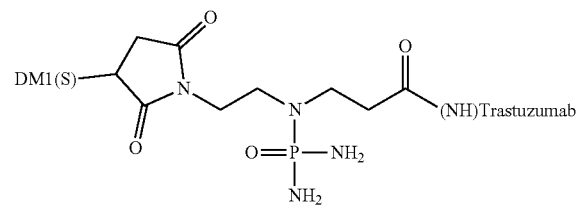
(Compound 63)
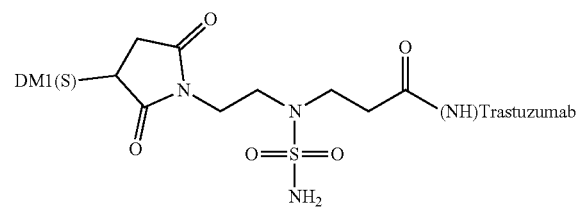
(Compound 64)
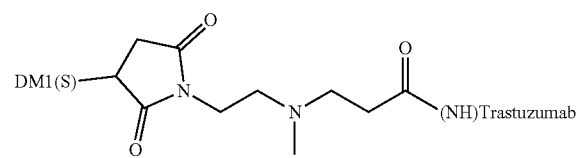
(Compound 65)
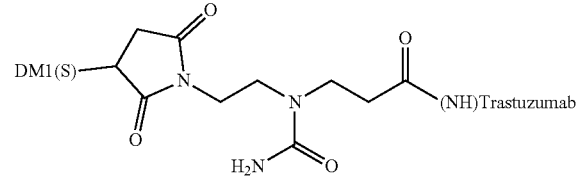
(Compound 66)
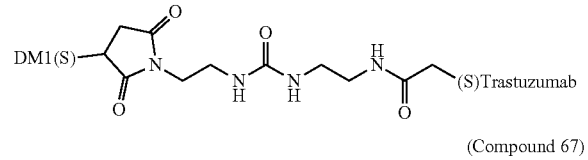
(Compound 67)
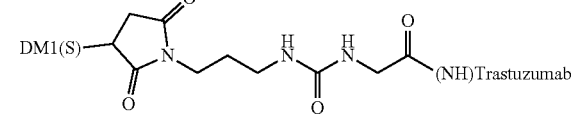
(Compound 68)
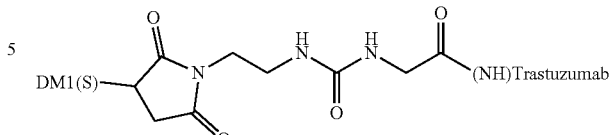
(Compound 69)
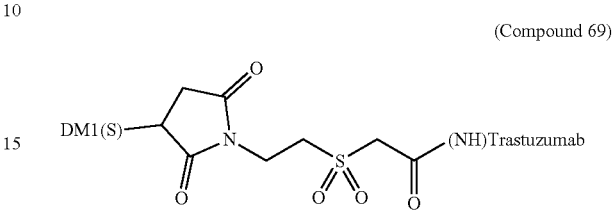
(Compound 70)
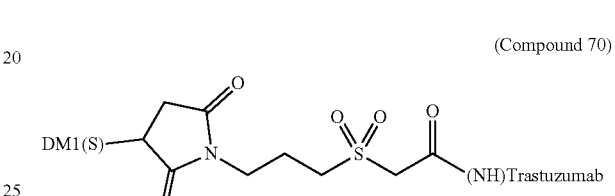
(Compound 71)
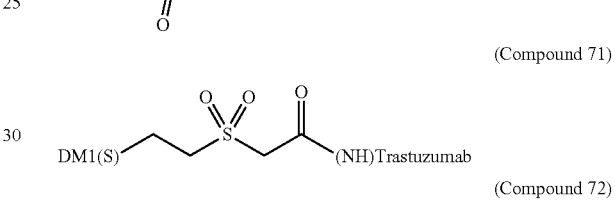
(Compound 72)
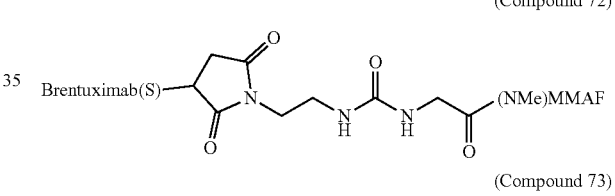
(Compound 73)
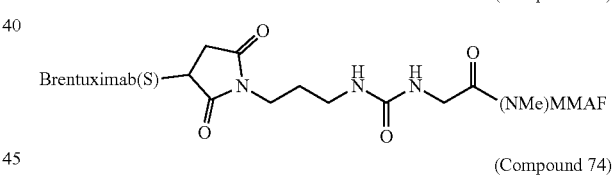
(Compound 74)
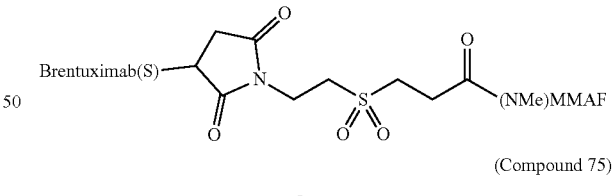
(Compound 75)
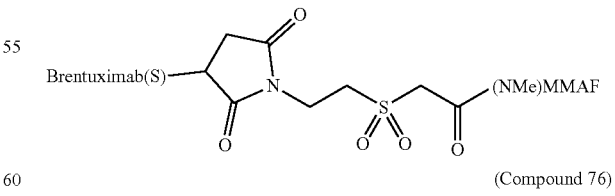
(Compound 76)
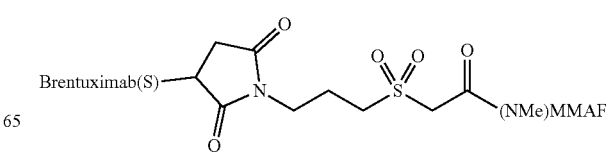

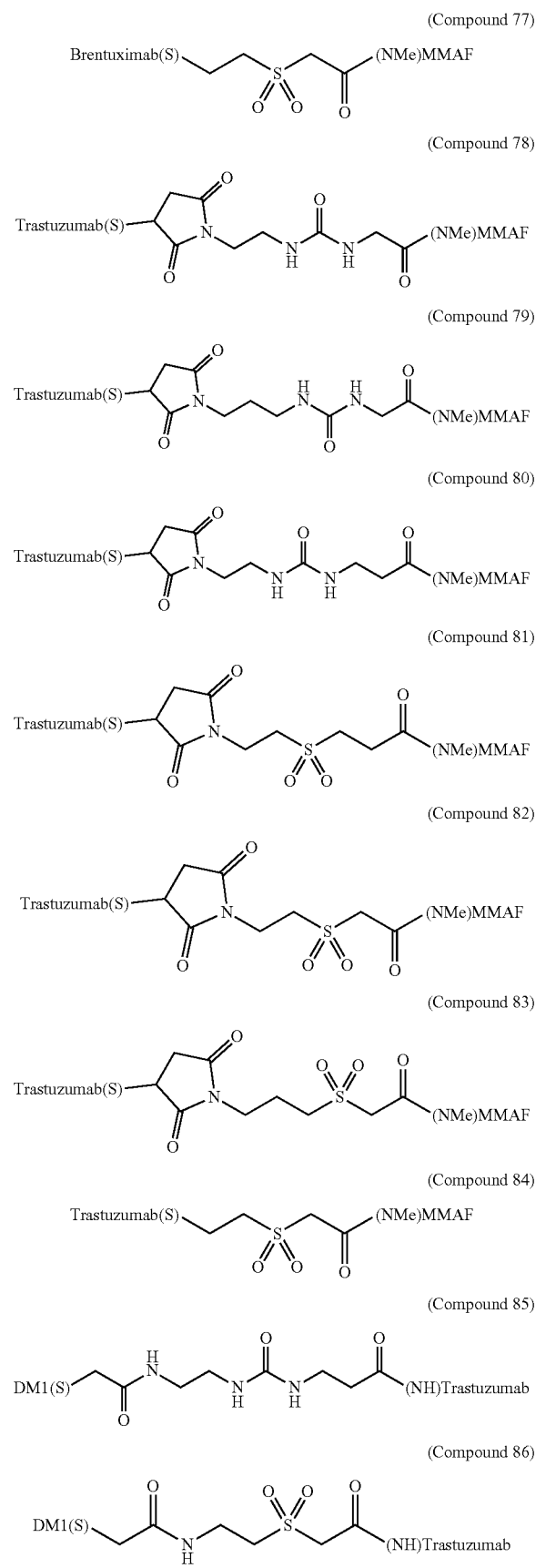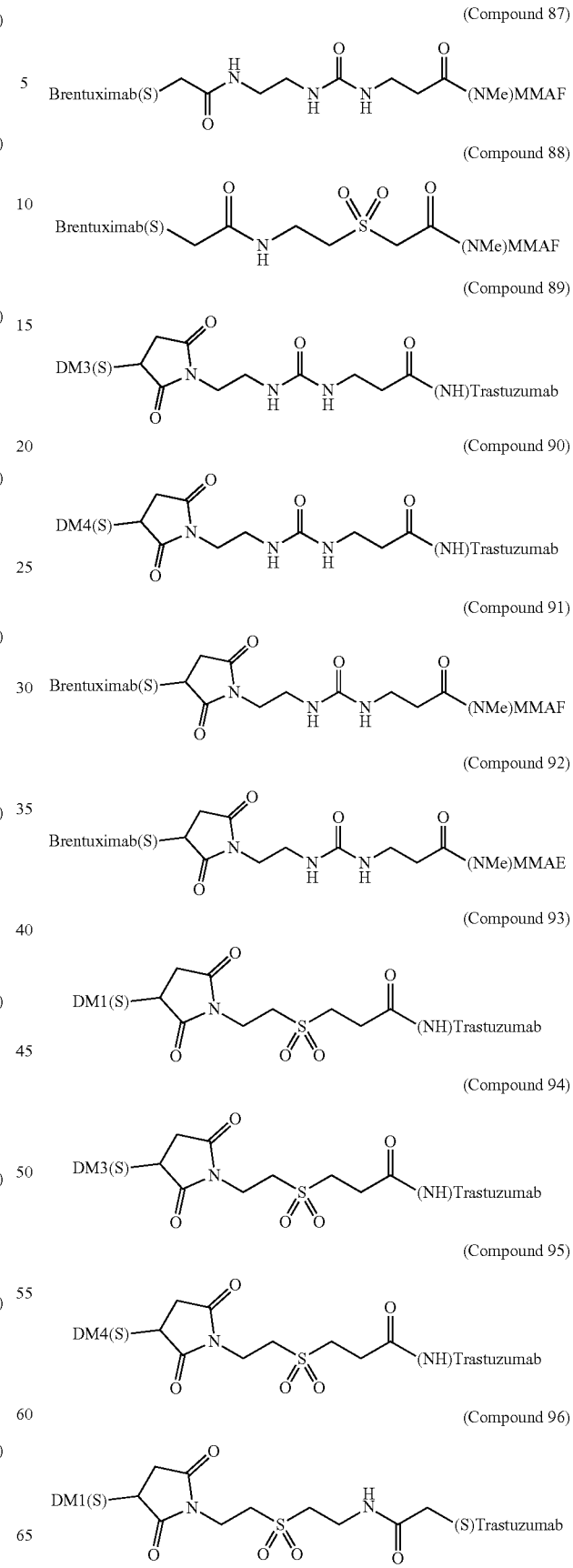

-continued (Compound 97)

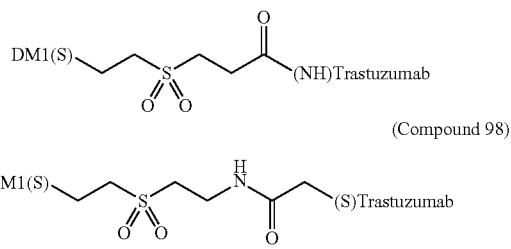

(Compound 98)

The above exemplary embodiments are used as illustrations of the invention. These embodiments are not intended to limit the scope of the invention. In fact, the invention is intended to cover all alternatives, modifications, and equivalents of these embodiments. It should not be understood that the present invention is only limited to the illustrated examples.

Preparation of the Ligand-Drug Conjugates

The ligand-drug conjugates of the present invention may be prepared by linking together the drug moiety, the hydrophilic linker moiety, and the ligand moiety using various synthetic techniques. Among all the approaches, it is advantageous to preinstall a suitable reactive functional group at each terminus of the hydrophilic linker. The preinstalled functional groups at the two termini of the hydrophilic linker are used for covalent coupling to the drug moiety and the cell-binding ligand moiety. The preinstalled functional groups will make the preparation of the ligand-drug conjugates an easily achievable process.

Accordingly, the ligand-drug conjugate of the present invention may be constructed by preparing the hydrophilic linker first. In the second step, the hydrophilic linker is coupled to the cytotoxic drug via either an inheterent or an introduced functional group such as an amino or thiol group on the drug to give a drug-linker adduct. The drug-linker adduct is then coupled to the cell-binding ligand such as an antibody that possesses suitable functional groups, such as the amino groups on lysine residues or the thiol groups on cysteine residues, for covalent coupling to give the intended ligand-drug conjugate.

Alternatively, the ligand-drug conjugate may be prepared by coupling the hydrophilic linker to the cell-binding ligand such as an antibody that possesses suitable functional groups, such as the amino groups on lysine residues or the thiol groups on cysteine residues, to give a ligand-linker adduct first. Next, the ligand-linker adduct is coupled to the cytotoxic drug via either an inheterent or an introduced functional group such as an amino or thiol group on the drug to give the ligand-drug conjugate as end product.

Useful functional groups on the cell-binding ligand such as an antibody for coupling to a hydrophilic linker include, but are not limited to, thiol, amino, hydroxyl, and carboxyl groups. In order to use a cell-binding ligand for the preparation of ligand-drug conjugate, it may be necessary to modify the ligand such as an antibody so that suitable functional groups are made available for coupling to the hydrophilic linker. For example, antibodies do not generally contain free thiols. However, the thiol group may be generated by reduction of either the native intramolecular cysteine disulfide bonds or chemically incorporated disulfide groups (e.g., SPDP may be used to incorporate disulfide groups) of an antibody using a mild reducing agent such as DTT, by derivatizing the amino group of a lysine residue using 2-iminothiolane (Traut's reagent), methyl 3-mercaptopropionimidate ester or other thiol generating reagents, or by introducing additional non-native cysteine residues on to the antibody using molecular biology techniques.

Useful functional groups on the cell-binding ligand such as an antibody for coupling to a hydrophilic linker may also be an aldehyde, acetal, or ketal group on a carbohydrate residue of a glycosylated antibody. The carbohydrate residue may be mildly oxidized using a reagent such as sodium periodate to generate a carbonyl group, which may be coupled to a hydrophilic linker that contains a suitable functional group, such as amino, hydrazine, hydrazide, thiosemicarbazone, or acylhydrazide.

The ligand-drug conjugates of the present invention in which the hydrophilic linker and ligand are linked via a thioether bond may be prepared by coupling a thiol group on the ligand to a thiol-reactive group (such as haloacetamide, maleimide, alkenyl sulfonyl group, or reactive disulfide group) on the hydrophilic linker. For example, for the preparation of an antibody-drug conjugate in which MMAF is used as the cytotoxic drug, a reduced antibody with its freed thiol groups may react with a maleimide containing hydrophilic linker to form a thioether linkage between the antibody and the linker. In the next step, the antibody-linker adduct, which may possess a preinstalled N-hydroxysuccinimide ester, may react with MMAF to give the desired antibody-drug conjugate.

The ligand-drug conjugates of the present invention in which the hydrophilic linker is coupled to the ligand via an amide group may be prepared by coupling a free amino group on the ligand to an activated carboxyl group on the hydrophilic linker. For example, a carboxyl group activated by forming N-hydroxysuccinimide ester may react with a free amino group on a lysine residue in the coupling reaction. The formed linkage between the ligand and the linker thereafter is an amide bond.

The advantage of using lysine or cysteine for the preparation of antibody-drug conjugate is that it is highly convenient. Of course, other than using the innate functional groups, artificially introduced functional groups may also be used for the preparation of antibody-drug conjugates of the present invention. Any method can be used to introduce a useful functional group at a suitable site of an antibody. These methods include, but are not limited to, the incorporation of an unnatural amino acid through genetic engineering (e.g., the incorporation of an amino acid with a carbonyl group and coupling to the linker via the carbonyl group), the incorporation of engineered glutamine residues and coupling to the linker by using microbial transglutaminase (mTG), the site-specific modification of heavy-chain C termini by intein fusion, and the site-specific incorporation of engineered cysteines.

Generally speaking, after the cell-binding ligand, such as an antibody, is covalently coupled to a hydrophilic linker at suitable positions, such as via the amino groups on lysine residues or the thiol groups on cysteine residues, a purification step (e.g., dialysis or gel filtration) is needed to separate the desired ligand-linker adduct from the unreacted portion of the hydrophilic linker. Next, after a cytotoxic drug that possesses a suitable functional group is coupled to the ligand-linker adduct obtained in the first step, an additional purification step (e.g., dialysis, gel filtration, ion-exchange chromatography, hydrophobic interaction chromatography, or combinations of them) may also be needed to remove the unreacted portion of the drug and the byproducts from the final antibody-drug conjugate.

Due to the hydrophobic nature of the cytotoxic drugs such as DM1 and DM4, it may be necessary to carry out the conjugation to the cell-binding ligand such as antibody in a mixture of aqueous buffer and organic solvent. The purpose is to ensure that the cytotoxic drug remains in solution during the conjugation process. Suitable organic solvents include methanol, ethanol, N,N-dimethylacetamide (DMA), N,N-dimethylformamide (DMF) and dimethyl sulfoxide (DMSO). The preferred amount of organic solvent in the aqueous buffer is 0-30% (v/v). The conjugation may be carried out at pH 5-9, more preferably at pH 6-8. The buffers used for the conjugation reaction are buffers with pKa values around this pH range. A large excess (5-50 fold) of the drug moiety over the cell-binding ligand such as antibody may be used in the conjugation reaction in order to obtain a conjugate with the desired number of drug molecules in each antibody molecule.

An exemplary process for preparing the ligand-drug conjugates of the present invention in which the ligand is an antibody is as follows: First, a hydrophilic linker that possesses both an NHS ester group and a maleimide group at the two termini is dissolved in N,N-dimethylacetamide (DMA) at approximately 20 mM. Next, the solution of an antibody (8 mg/mL) is treated with 5-50 equiv of the hydrophilic linker in a sodium phosphate buffer (pH=6-8, 5% DMA by volume). The reaction is allowed to proceed at ambient temperature for 10 min to 24 h. The unreacted portion of the hydrophilic linker is removed from the antibody by gel filtration using a Sephadex G25 column equilibrated in 150 mM potassium phosphate buffer containing 100 mM NaCl. For the conjugation reaction, a thiol-containing maytansinoid, such as DM1 or DM4, is dissolved in DMA at approximately 10 mM. Then, the maytansinoid (1-2 equiv of the hydrophilic linker) is slowly added to the antibody-linker adduct (2.5 mg/mL) in sodium phosphate buffer (pH=6.5-7.0, 3% DMA by volume) at stirring. The reaction is allowed to proceed at ambient temperature for 2-12 h. The formed antibody-drug conjugate is purified using a Sephadex G25 column equilibrated with sodium phosphate buffer (pH=6.5). The number of maytansinoid molecules incorporated in each antibody molecule is assessed by measuring A252 and A280 of the antibody-drug conjugate (Zhao, et al., J. Med. Chem., 2011, 54, 3606~3623).

An exemplary one-step process for preparing the ligand-drug conjugates of the present invention in which the ligand is an antibody is as follows: The solution of a hydrophilic linker (1.0 equiv) that possesses both an NHS ester group and a maleimide group at the two termini in N,N-dimethylacetamide (DMA) is added to a PBS buffer (pH=6.0) that contains a maytansinoid drug, such as DM1 or DM4 (1.5 equiv). The mixture is incubated for 45-120 min at 4-20° C. Then, a PBS buffer (pH=7-8) that contains a monoclonal antibody (0.1-0.25 equiv) is added to the drug-linker adduct. After incubating at room temperature for 2-24 h, the formed antibody-drug conjugate is purified using a Sephadex G25 column equilibrated with PBS (pH=6.5). The number of maytansinoid molecules incorporated in each antibody molecule is assessed by measuring A252 and A280 of the antibody-drug conjugate.

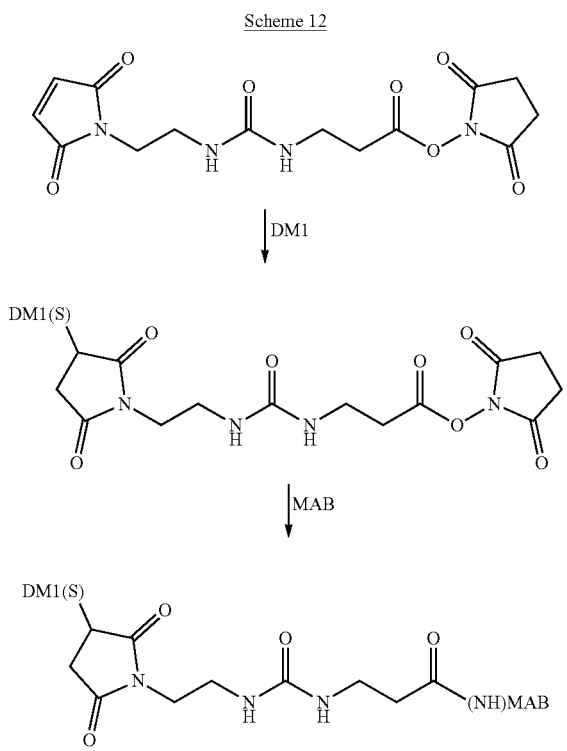

Scheme 12

As a more specific embodiment of the present invention, in the first step, a thiol-containing maytansinoid drug (DM1) reacts with a hydrophilic linker to give a drug-linker adduct by forming a thioether bond. Next, the drug-linker adduct reacts with the amino groups of lysine residues on an antibody (MAB) to provide an antibody-drug conjugate as the final product (Scheme 12).

Alternatively, the antibody (MAB) can first react with the hydrophilic linker to give an antibody covalently bonded to the linker via amide bond. In the next step, the maytansinoid drug (DM1) reacts with the maleimido functional group at the other terminus of the hydrophilic linker to give the same antibody-drug conjugate (Scheme 13).

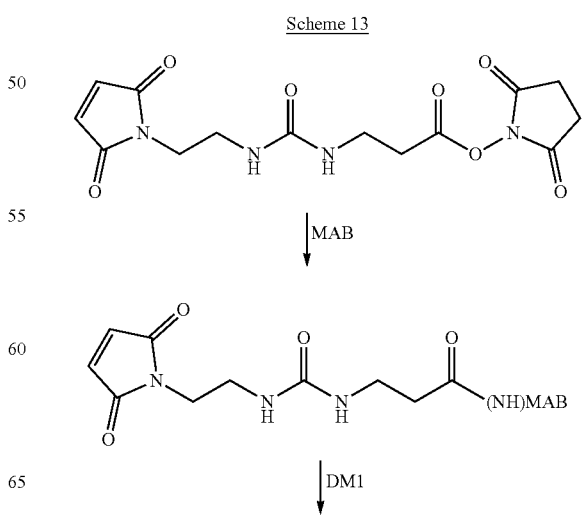

Scheme 13

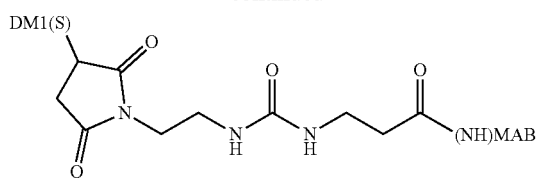

Scheme 14

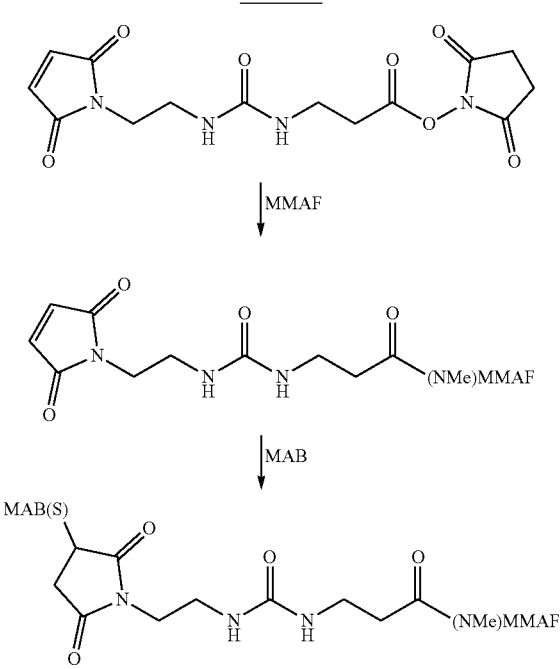

In another embodiment of the present invention (Scheme 14), an auristatin drug (MMAF) is coupled to a hydrophilic linker through an amide bond first. Then, a monoclonal antibody (MAB) is conjugated to the drug-linker adduct to give an antibody-drug conjugate as the final product.

In an alternative embodiment of the present invention (Scheme 15), a maytansinoid drug (DM1) reacts with a semi-ready hydrophilic linker first. Then, after the needed functional group (NHS ester) is introduced at the other terminus of the hydrophilic linker, the drug-linker adduct is coupled to a monoclonal antibody (MAB) via the amino groups on lysine residues of the antibody to give the antibody-drug conjugate as the final product.

Scheme 15

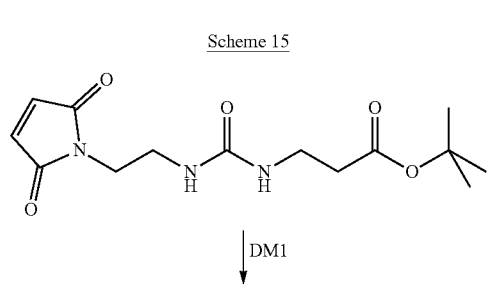

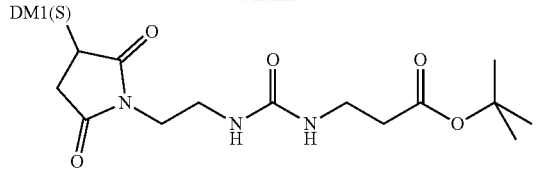

One skilled in the art will realize that the same ligand-drug conjugate of the present invention can be synthesized by many different methods. For example, instead of directly using hydrophilic linkers that already possess one or two suitable functional groups for crosslinking purpose, the hydrophilic linker may also be constructed step by step during the conjugation process, starting from either the cytotoxic drug or the cell-binding ligand. Or, the hydrophilic linker can be constructed step by step starting from both the cytotoxic drug and the cell-binding ligand. After the two growing portions of the hydrophilic linker are joined together, the preparation of the ligand-drug conjugate is also complete.

EXAMPLES

The following examples, which are for detailed illustration only, are not intended to limit the scope of the present invention.

Example 1

3-(2-Chloro-ethanesulfonyl)-propionic Acid

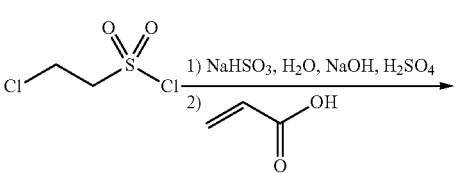

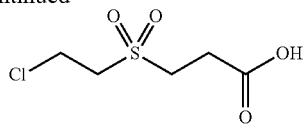

Step 1: A 2 L round bottom flask charged with NaHSO₃ (83 g, 0.80 mol) and water (400 mL) were placed in an ice bath. 2-chloroethanesulfonyl chloride (120 g, 0.74 mol) and a solution of NaOH (83 g, 2.08 mol) in water (210 mL) were added slowly at the same time as the contents of the flask was stirred for 1 h. After 0.5 h of stirring, 50% H₂SO₄ (70 mL, 0.37 mol) was added. The solution was stirred for 1 h at 0~5° C. Then the reaction mixture was filtered and the filtrate was used of the next step.

Step 2: A solution of acrylic acid (55 g, 0.76 mol) in water (100 mL) was added to the above filtrate and the mixture was stirred for 10 min. It was placed in a refrigerator for 3 days at 4° C. The mixture was filtered and the residual solid was recrystallized from hot water to give a white powder (50 g, 0.25 mol, 33.7% yield). ¹H NMR (500 MHz, MeOD): δ 3.96 (dd, J=8.6, 5.4 Hz, 2H), 3.63 (t, J=7.0 Hz, 2H), 3.49 (t, J=7.3 Hz, 2H), 2.87-2.82 (m, 2H).

Example 2

3-(2-Chloro-ethanesulfonyl)-propionyl Chloride

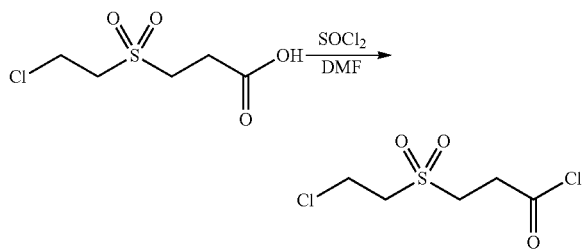

To a solution of 3-(2-chloroethylsulfonyl)propionyl acid (16.0 g, 80.0 mmol) in thionyl chloride (100 ml) was added DMF (0.5 mL). The mixture was heated at the reflux for 2 h. Then, it was concentrated to afford the title compound (15.8 g, 90.2% yield) as a yellow solid, which was used without further purification.

Example 3

3-(2-Chloro-ethanesulfonyl)-propionic acid 2,5-dioxo-pyrrolidin-1-yl Ester

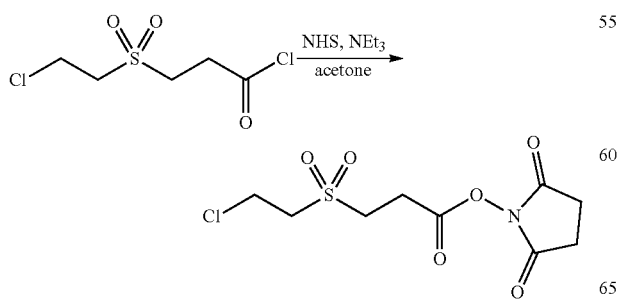

N-Hydroxysuccinimide (6.0 g, 52.1 mmol) was added to triethylamine (5.5 mL, 44 mmol) and acetone (150 mL) in an ice bath. 3-(2-chloroethylsulfonyl)propionyl chloride (9.5 g, 43.3 mmol) in acetone (50 mL) was then added dropwise, and the resulting suspension was stirred for 3 h. Next, the ice bath was removed and it was stirred for an additional 30 min. It was concentrated to about 100 mL. The resulting mixture was poured into ice water (1000 mL) and stirred for 3 min. The precipitate was collected by filtration and dried under vacuum to give the title compound as a white powder (10.3 g, 80% yield). ¹H NMR (500 MHz, MeOD): δ 3.94 (d, J=6.9 Hz, 2H), 3.66 (d, J=6.9 Hz, 2H), 3.59 (d, J=7.5 Hz, 2H), 3.23 (d, J=7.5 Hz, 2H), 2.84 (s, 4H).

Example 4

3-Ethenesulfonyl-propionic acid 2,5-dioxo-pyrrolidin-1-yl Ester

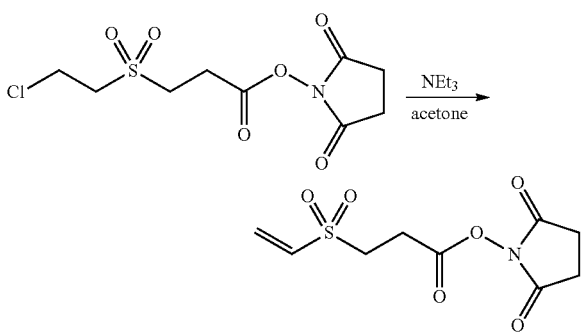

To a solution of 3-(2-chloro-ethanesulfonyl)-propionic acid 2,5-dioxo-pyrrolidin-1-yl ester (2.41 g, 8.1 mmol) in acetone (50 mL) was added triethylamine (1.5 mL, 10.8 mmol) in an ice bath. The resulting reaction mixture was slowly warmed to room temperature and stirred overnight. Next, the mixture was concentrated under reduced pressure, the residue was purified by column chromatography (from CH₂Cl₂ to CH₂Cl₂/MeOH, 15:1) to afford the title compound (2.01 g, 7.69 mmol, 95.0% yield) as a white powder. ¹H NMR (500 MHz, MeOD): δ 6.86 (dd, J=16.6, 10.0 Hz, 1H), 6.42 (d, J=16.6 Hz, 1H), 6.28 (d, J=9.9 Hz, 1H), 3.50 (t, J=7.4 Hz, 2H), 3.12 (t, J=4.2 Hz, 2H), 2.84 (s, 4H). MS m/z+ for [C₉H₁₁NO₆S] (M+H) cald: 262.03; found: 262.0251.

Example 5

3-Ethenesulfonyl-propionic acid 2,5-dioxo-pyrrolidin-1-yl Ester

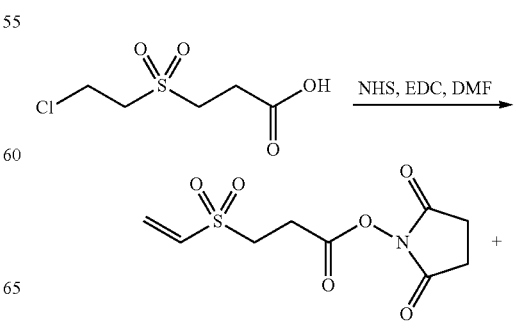

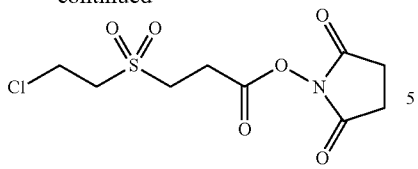

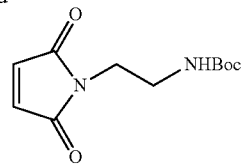

To a solution of 3-(2-chloroethylsulfonyl)propionyl acid (3.59 g, 17.9 mmol) in DMF (50 mL) was added N-hydroxysuccinimide (3.09 g, 26.8 mmol) and 1-ethyl-3-(3-dimethylaminopropyl)carbodiimide hydrochloride (6.80 g, 35.8 mmol) in an ice bath. The resulting solution was warmed to room temperature over 15 min. After stirring for 3 h, the mixture was concentrated under reduced pressure, the residue was purified by column chromatography (from $CH_2Cl_2$ to $CH_2C2/MeOH=15:1$) to afford 3-ethenesulfonyl-propionic acid 2,5-dioxo-pyrrolidin-1-yl ester (2.87 g, 11.0 mmol, 61.5% yield) as a white powder. The reaction also afforded 3-(2-chloro-ethanesulfonyl)-propionic acid 2,5-dioxo-pyrrolidin-1-yl ester as a minor product (0.84 g, 2.82 mmol, 15.8% yield, see Example 3).

Example 6

2,5-Dioxo-2,5-dihydro-pyrrole-1-carboxylic Acid Methyl Ester

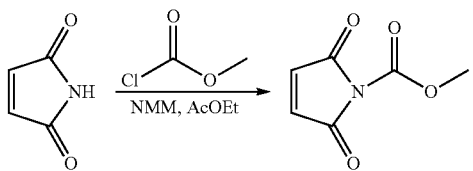

Maleimide (12.0 g, 123.7 mmol) was dissolved in ethyl acetate (150 mL) in a 250 mL round-bottom flask, and the solution was cooled to approximately 0° C. A solution of N-methyl morpholine, (14.1 mL, 12.8 g, 126.2 mmol) in ethyl acetate (10 mL) was added dropwise over 15 min. A solution of methyl chloroformate (9.60 mL, 11.5 g, 123.7 mmol) in ethyl acetate (50 mL) was added dropwise, and the solution was warmed to room temperature and stirring for 2 h. The solution was diluted with ethyl acetate (100 mL) and washed with saturated aqueous sodium bicarbonate solution, water, and saturated sodium chloride solution. The organic layer was separated, dried over $Na_2SO_4$, and filtered. The supernatant was concentrated under reduced pressure to yield the title compound as a solid (15.9 g, 102.5 mmol, 82.9% yield). $^1H$ NMR (500 MHz, $CDCl_3$): δ 6.84 (s, 2H), 3.97 (s, 3H).

Example 7

[2-(2,5-Dioxo-2,5-dihydro-pyrrol-1-yl)-ethyl]-carbamic Acid Tert-Butyl Ester

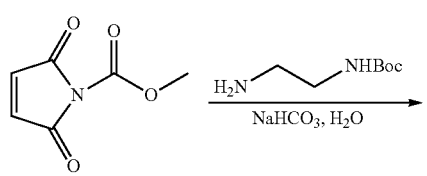

N-Boc-ethylenediamine (2.0 g, 12.48 mmol) was dissolved in a saturated solution of $NaHCO_3$ (50 mL) and cooled to 0° C. N-(methoxycarbonyl)maleimide (1.9 g, 12.25 mmol) was added to the stirred solution. After 10 mins the reaction mixture was diluted with water (100 mL) and stirred for 30 min at room temperature. The reaction mixture was cooled to 0° C., and the reaction mixture was filtered and washed with ice-cold water (100 mL). Drying in high vacuum afforded the title compound (2.35 g, 9.78 mmol, 78.4% yield) as a white solid. $^1H$ NMR (500 MHz, $CDCl_3$): δ 6.71 (s, 2H), 4.72 (s, 1H), 3.69-3.62 (m, 2H), 3.34 (d, J=5.1 Hz, 2H), 1.41 (s, 9H).

Example 8

1-(2-Amino-ethyl)-pyrrole-2,5-dione Hydrochloride

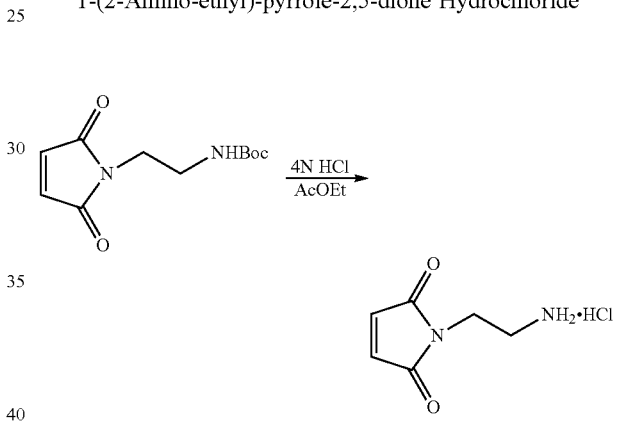

N-(2-((tert-Butoxycarbonyl)amino)ethyl)maleimide (750 mg, 3.12 mmol) was dissolved in 4 M HCl in ethyl acetate (20 mL) and stirred for 8 h at room temperature. Then, addition of diethyl ether at 0° C. provided the title compound as a white precipitate (524 mg, 2.97 mmol, 95.2% yield). $^1H$ NMR (500 MHz, MeOD): δ 6.90 (s, 2H), 3.83-3.79 (m, 2H), 3.17-3.13 (m, 2H).

Example 9

3-Isocyanato-propionic Acid Tert-Butyl Ester

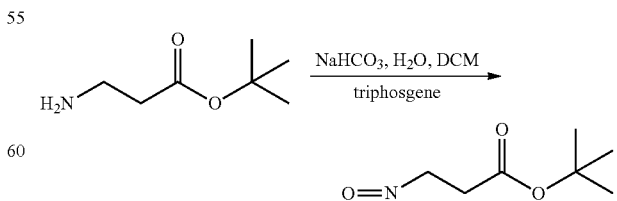

Triphosgene (940 mg, 3.20 mmol) was added to a mixture of 1,1-dimethylethyl ester hydrochloride (820 mg, 4.50 mmol) in $CH_2Cl_2$ (20 mL) and saturated $NaHCO_3$ (20 mL). The reaction was stirred at 0° C. for 30 minutes. The organic phase was separated and the aqueous phase was extracted with CH$_2$Cl$_2$ (2×20 mL). The combined organic phase was dried (Na$_2$SO$_4$), filtered and concentrated under vacuum to give a thin oil which was used without purification for the next reaction.

Example 10

3-{3-[2-(2,5-Dioxo-2,5-dihydro-pyrrol-1-yl)-ethyl]-ureido}-propionic Acid Tert-Butyl Ester

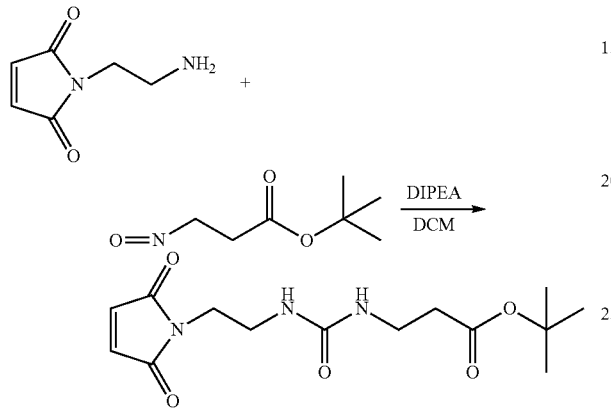

N-(2-Aminoethyl)maleimide hydrochloride (635.7 mg, 3.60 mmol) was dissolved in CH$_2$Cl$_2$ (20 mL) and DIPEA (1.5 mL, 88.1 mmol), and the solution was cooled to approximately 0° C. A solution of 3-isocyanato-1,1-dimethylethyl ester (prepared in the previous step) in CH$_2$Cl$_2$ (10 mL) was added. The resulting mixture was stirred for 10 min at room temperature. The reaction was concentrated under vacuum. Purification of the residue by column chromatography (from CH$_2$Cl$_2$ to CH$_2$C2/MeOH=15:1) afforded the title compound (910 mg, 2.93 mmol, 71.4% yield) as a white powder. $^1$H NMR (500 MHz, CDCl$_3$): δ 6.71 (s, 2H), 3.68-3.64 (m, 2H), 3.41-3.38 (m, 2H), 3.37 (t, J=5.9 Hz, 2H), 2.42 (t, J=5.7 Hz, 2H), 1.44 (s, 9H). MS m/z+ for [C$_{14}$H$_{21}$N$_3$O$_5$] (M+H) cald: 312.33; found: 312.1590.

Example 11

3-{3-[2-(2,5-Dioxo-2,5-dihydro-pyrrol-1-yl)-ethyl]-ureido}-propionic Acid

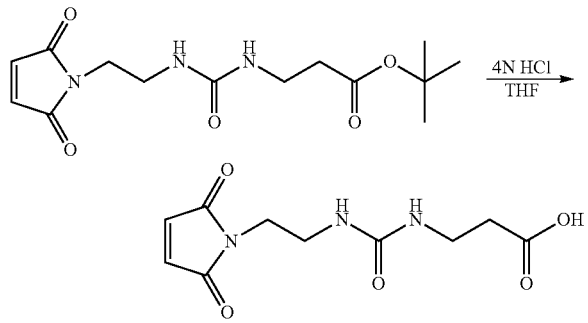

3-{3-[2-(2,5-Dioxo-2,5-dihydro-pyrrol-1-yl)-ethyl]-ureido}-propionic acid tert-butyl ester (458 mg, 1.47 mmol) was dissolved in 4 M HCl in CH$_2$Cl$_2$ (10 mL) and stirred for 8 h at room temperature. After the mixture was concentrated under vacuum, addition of CH$_2$Cl$_2$ at 0° C. provided the title compound as a white precipitate (352 mg, 1.38 mmol, 93.9% yield), which was used without purification for the next reaction.

Example 12

3-{3-[2-(2,5-Dioxo-2,5-dihydro-pyrrol-1-yl)-ethyl]-ureido}-propionic acid 2,5-dioxo-pyrrolidin-1-yl Ester

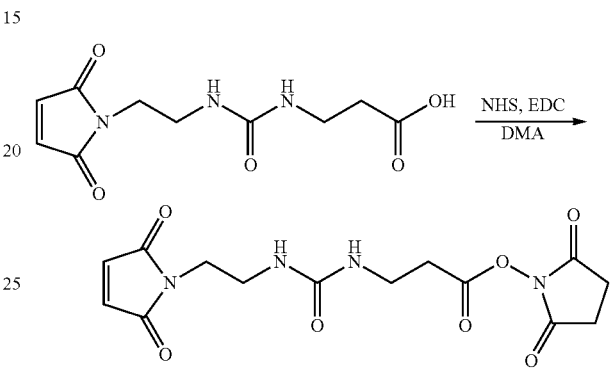

To N-[[(3-maleimido)ethyl]amino]carbonyl-(3-alanine (55 mg, 0.216 mmol) in DMA (5 ml) was added N-hydroxysuccimide (25 mg, 0.217 mmol) and EDC (100 mg, 0.526 mmol). The mixture was stirred overnight at room temperature. The mixture was concentrated under reduced pressure. The residue was purified by column chromatography (from CH$_2$Cl$_2$ to CH$_2$Cl$_2$/EtOAc=9:1) to afford the title product (69.7 mg, 198 mmol, 91.7% yield) as a white solid. $^1$H NMR (500 MHz, CDCl$_3$): δ 6.70 (s, 2H), 3.64-3.59 (m, 2H), 3.53 (t, J=5.8 Hz), 3.38 (t, J=5.6 Hz, 2H), 2.86 (s, 4H), 2.78 (t, J=5.8 Hz, 2H). MS m/z+ for [C$_{14}$H$_{16}$N$_4$O$_7$] (M+H) cald: 353.30; found: 353.1070.

Example 13

(3-Hydroxy-propylsulfanyl)-acetic Acid Tert-Butyl Ester

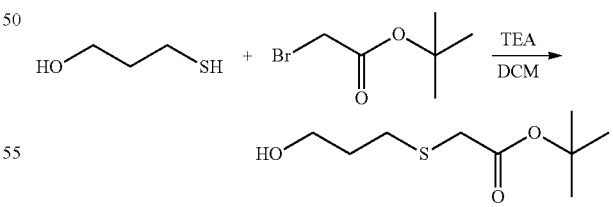

tert-Butyl bromoacetate (3.0 g, 15.4 mmol) and triethylamine (3.2 g, 31.8 mol) were dissolved in CH$_2$Cl$_2$ (30 mL) under nitrogen and cooled to 0° C. 3-Mercapto-1-ethanol (1.48 g, 16.0 mol,) was slowly added to the mixture and the reaction mixture was warmed to room temperature. The reaction was stirred for 1 additional hour. Completion of the reaction was monitored by TLC (ethylacetate/hexane=1:1 (v/v), Rt=0.80). The solution was washed with saturated aqueous sodium bicarbonate solution (30 mL×2), water, and saturated sodium chloride solution. The organic layer was separated, dried over Na₂SO₄, and filtered. The supernatant was concentrated under reduced pressure to yield the title compound as a colorless oil (2.53 g, 79.8% yield). $^1$H NMR (500 MHz, CDCl₃): δ (ppm) 3.74 (t, J=6.0 Hz, 2H), 3.13 (s, 2H), 2.74 (t, J=7.1 Hz, 2H), 1.87-1.82 (m, 2H), 1.45 (s, 9H).

Example 14

(3-Hydroxy-propane-1-sulfonyl)-acetic Acid Tert-Butyl Ester

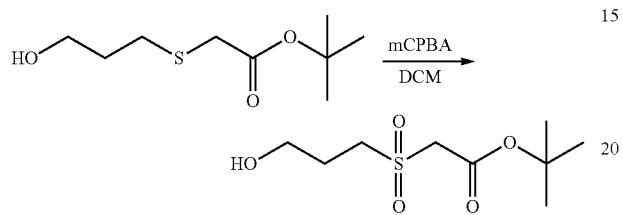

(3-Hydroxy-propylsulfanyl)-acetic acid tert-butyl ester (3.70 g, 17.96 mmol) was dissolved in dry DCM (70 mL) and cooled to −10° C. To the stirred reaction mixture was added mCPBA (7.4 g, 42.88 mmol) slowly over 30 minutes and the mixture was stirred for a further 48 h at room temperature. Next, Na₂S₂O₃ (10 mL, sat.) and Na₂CO₃ (10 mL, sat.) were added and the reaction stirred for 2 h at room temperature. The solution was washed with 1M NaOH solution (30 mL×2), saturated aqueous sodium bicarbonate solution, and saturated sodium chloride solution. The organic phase was dried over Na₂SO₄. After evaporation of the solvent, the crude material was purified by silica gel flash chromatography (DCM/MeOH=50:1) to give the title compound as a colorless oil (3.85 g, 89.8% yield). $^1$H NMR (500 MHz, CDCl₃): δ (ppm) 3.84 (s, 2H), 3.61 (t, J=6.0 Hz, 2H), 3.30-3.23 (m, 2H), 1.99-1.90 (m, 2H), 1.38 (s, 9H).

Example 15

[3-(3,5-Dioxo-10-oxa-4-aza-tricyclo[5.2.1.0²,⁶]dec-8-en-4-yl)-propane-1-sulfonyl]-acetic Acid Tert-Butyl Ester

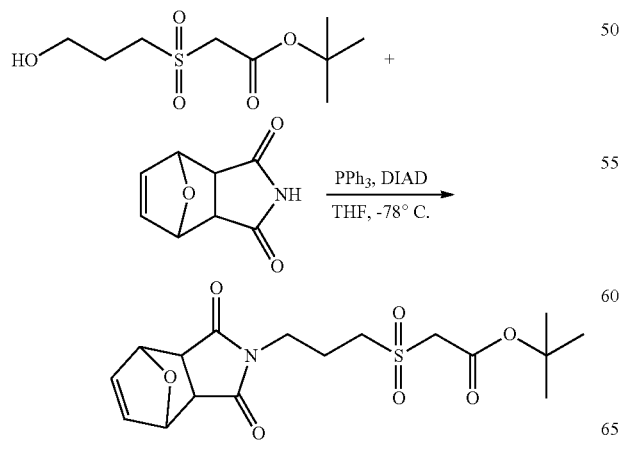

A mixture of triphenylphosphine (1.57 g, 6.0 mmol), 2,2-dimethypropan-1-ol (0.3 g, 3.5 mmol), (3-hydroxy-propane-1-sulfonyl)-acetic acid tert-butyl ester (1.50 g, 6.3 mmol) and 7-oxabicyclo(2.2.1)hept-5-ene-2,3-dicarboximide (1.00 g, 5.7 mmol) was dissolved in THF (20 mL) at −78° C. under N₂, and the result mixture was stirred for 5 min. To the reaction mixture was added DIAD (1.9 M in toluene, 3.0 mL). After being stirred for 15 min, the reaction mixture was allowed to warm slowly to room temperature and stirred overnight. Then, the mixture was concentrated under reduced pressure. The residue was purified by column chromatography (from CH₂Cl₂ to CH₂Cl₂/EtOAc=10:1) to afford the title compound (1.03 g, 46.9% yield) as a white solid. $^1$H NMR (500 MHz, CDCl₃): δ (ppm) 6.47 (s, 2H), 5.22 (s, 2H), 3.83 (s, 2H), 3.60 (t, J=6.7 Hz, 2H), 3.23-3.18 (m, 2H), 2.84 (s, 2H), 2.14-2.07 (m, 2H), 1.46 (s, 9H).

Example 16

[3-(2,5-Dioxo-2,5-dihydro-pyrrol-1-yl)-propane-1-sulfonyl]-acetic Acid Tert-Butyl Ester

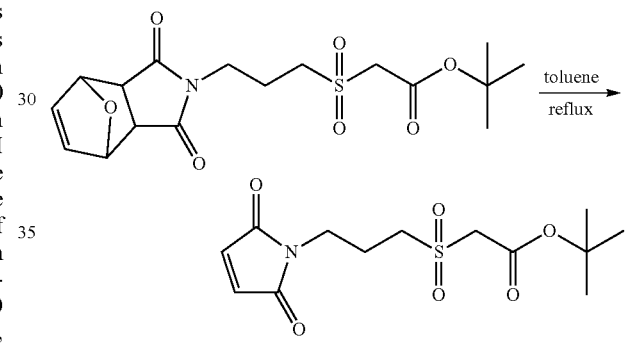

A stirred solution of [3-(3,5-dioxo-10-oxa-4-aza-tricyclo[5.2.1.0²,⁶]dec-8-en-4-yl)-propane-1-sulfonyl]-acetic acid tert-butyl ester (0.50 g, 1.30 mmol) in toluene (20 mL) was heated at reflux overnight. The mixture was concentrated under reduced pressure, and the residue was purified by column chromatography (n-Hex/EtOAc=10:1) to afford the desired product (0.38 g, 92.1% yield) as a white solid. $^1$H NMR (500 MHz, CDCl₃): δ (ppm) 6.73 (s, 2H), 3.85 (s, 2H), 3.69 (t, J=6.7 Hz, 2H), 3.29-3.24 (m, 2H), 2.84 (s, 2H), 2.20-2.14 (m, 2H), 1.49 (s, 9H).

Example 17

[3-(2,5-Dioxo-2,5-dihydro-pyrrol-1-yl)-propane-1-sulfonyl]-acetic Acid

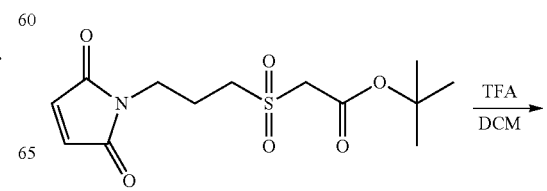

-continued

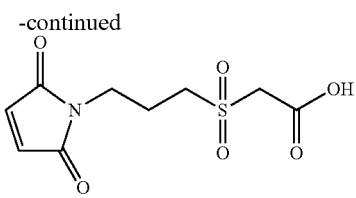

[3-(2,5-Dioxo-2,5-dihydro-pyrrol-1-yl)-propane-1-sulfonyl]-acetic acid tert-butyl ester (0.35 g, 1.10 mmol) was dissolved in TFA (5 mL) in $CH_2Cl_2$ (10 mL) and stirred for 8 h at room temperature. After the mixture was concentrated under vacuum, addition of $CH_2Cl_2$ at 0° C. provided the title compound as a white precipitate (0.27 g, 94.0% yield), which was used without purification for the next reaction. $^1H$ NMR (500 MHz, $CDCl_3$): δ (ppm) 6.85 (s, 2H), 4.16 (s, 2H), 3.68 (t, J=6.7 Hz, 2H), 3.39-3.35 (m, 2H), 2.61-2.10 (m, 2H).

Example 18

[3-(2,5-Dioxo-2,5-dihydro-pyrrol-1-yl)-propane-1-sulfonyl]-acetic acid 2,5-dioxo-pyrrolidin-1-yl Ester

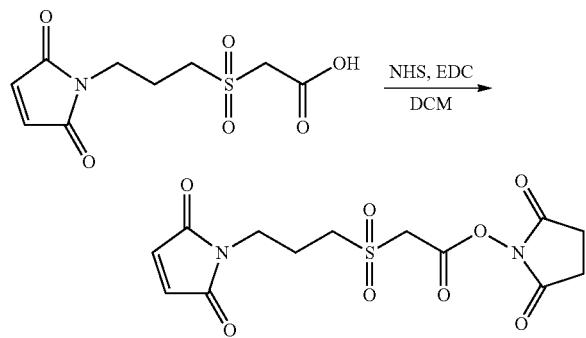

To [3-(2,5-Dioxo-2,5-dihydro-pyrrol-1-yl)-propane-1-sulfonyl]-acetic acid (130 mg, 0.50 mmol) in DCM (5 ml) was added N-hydroxysuccimide (69 mg, 0.60 mmol) and EDC (190 mg, 1.00 mmol). The mixture was stirred overnight at room temperature. The mixture was concentrated under reduced pressure, and the residue was purified by column chromatography (from $CH_2Cl_2$ to $CH_2Cl_2$/MeOH=10:1) to afford the desired product (151 mg, 84.6% yield) as a white solid. $^1H$ NMR (500 MHz, $CDCl_3$) δ (ppm) 6.71 (s, 2H), 3.65 (t, J=6.8 Hz, 2H), 3.38 (t, J=5.6 Hz, 2H), 3.32-3.26 (m, 2H), 2.71 (s, 4H), 2.16-2.07 (m, 2H).

Example 19

An Antibody-Drug Conjugate (DX-111)

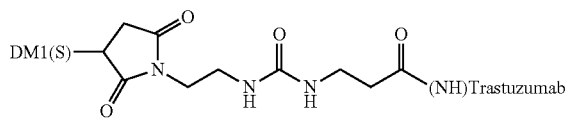

3-{3-[2-(2,5-Dioxo-2,5-dihydro-pyrrol-1-yl)-ethyl]-ureido}-propionic acid 2,5-dioxo-pyrrolidin-1-yl ester (Example 12) was dissolved in DMA (N, N-dimethylacetamide) at a concentration of approximately 10 mM. Trastuzumab (Herceptin) was dialyzed into a buffer (Buffer A: 50 mM $NaH_2PO_4$, 50 mM NaCl, 2 mM EDTA, pH 6.5). To couple the linker to the antibody, to a stirred solution of the antibody at 5 mg/ml were added 7 equivalents of the linker in a final concentration of 5% (v/v) DMA. The reaction was allowed to proceed at ambient temperature for 90 minutes. The unreacted linker was removed by gel filtration using a Sephadex G25 column equilibrated with Buffer A at pH 6.5. Then, a 10 mM solution of DM1 in DMA (1.5 equiv of the hydrophilic linker) was slowly added to a stirred solution of the antibody-linker adduct which was at a concentration of 2.5 mg/ml in Buffer A (pH 7.4) in a final concentration of 3% (v/v) DMA. The reaction was allowed to proceed at ambient temperature for 4 hours. The formed antibody-drug conjugate was purified by a Sephadex G25 column equilibrated with PBS (100 mM $NaH_2PO_4$, 50 mM NaCl, pH 6.5). The average number of drugs on each antibody was 3.5, which was assessed by measuring A254 and A280 of the conjugate (Zhao, et al., J. Med. Chem., 2011, 54, 3606-3623).

Example 20

An Antibody-Drug Conjugate (DX-112)

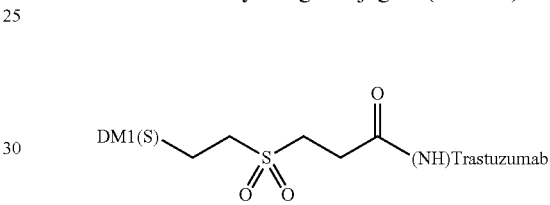

3-Ethenesulfonyl-propionic acid 2,5-dioxo-pyrrolidin-1-yl ester (Example 5) was dissolved in DMA (N, N-dimethylacetamide) at a concentration of approximately 10 mM. Trastuzumab (Herceptin) was dialyzed into a buffer (Buffer A: 50 mM $NaH_2PO_4$, 50 mM NaCl, 2 mM EDTA, pH 6.5). To couple the linker to the antibody, to a stirred solution of the antibody at 5 mg/ml were added 7 equivalents of the linker in a final concentration of 5% (v/v) DMA. The reaction was allowed to proceed at ambient temperature for 90 minutes. The unreacted linker was removed by gel filtration using a Sephadex G25 column equilibrated with 100 mM sodium phosphate buffer containing 100 mM NaCl, pH 7.4. Then, a 10 mM solution of DM1 in DMA (1.5 equiv of the hydrophilic linker) was slowly added to a stirred solution of the antibody-linker adduct which was at a concentration of 2.5 mg/ml in Buffer A (pH 7.4) in a final concentration of 3% (v/v) DMA. The reaction was allowed to proceed at ambient temperature for 4 hours. The formed antibody-drug conjugate was purified by a Sephadex G25 column equilibrated with PBS (100 mM $NaH_2PO_4$, 50 mM NaCl, pH 6.5). The average number of drugs on each antibody was 2.0, which was assessed by measuring A254 and A280 of the conjugate (Zhao, et al., J. Med. Chem., 2011, 54, 3606-3623).

Example 21

In Vitro Cytotoxicity Assay

The cell lines used in the cytotoxicity assays were HL-60, a human promyelocytic leukemia cell line; NCI-N87, a human gastric carcinoma cell line; BT-474, a human invasive ductal carcinoma cell line; and SKOV3, a human ovarian carcinoma cell line. For HL-60, NCI-N87, and BT-474 cells, the cells were grown in RPMI-1640 with 10%

FBS. For SKOV3 cells, the cells were grown in McCoy's 5A Medium with 10% FBS. To run the assay, the cells (180 μl, 6000 cells) were added to each well in a 96-well plate and incubated at 37° C. with 5% $CO_2$ for 24 hours. Next, the cells were treated with test compounds (20 py) at various concentrations in appropriate cell culture medium (total volume, 0.2 mL). The control wells contain cells and the medium but lack the test compounds. The plates were incubated at 37° C. with 5% $CO_2$ for 120 hours. MTT (5 mg/ml) was then added to the wells (20 μl) and the plates were incubated at 37° C. for 1.5 hr. The medium was carefully removed and DMSO (180 μl) was added afterward. After it

TABLE 1

| | | In Vitro Cytotoxicity Assay $IC_{50}$ (nM) | |
|---|---|---|---|
| | T-DM1 | DX-111 | DX-112 |
| Her2− HL-60 | >10,000 | >10,000 | >10,000 |
| Her2++ N87-3 | 0.89 | 0.78 | 0.82 |
| Her2++ BT474 | 0.78 | 0.53 | 0.72 |
| Her2++ SKOV3 | 0.20 | 0.20 | 0.16 | was shaken for 15 min, the absorbance was measured at 490 nm and 570 nm with a reference filter of 620 nm. The inhibition % was calculated according to the following equation: inhibition %=[1-(assay-blank)/(control-blank)]× 100. For DX-111, DX-112, and T-DM1, the results of the in vitro cytotoxicity assays were shown in Table 1.

Example 22

In Vivo Assay:

Target-positive xenograft tumor was established by subcutaneous inoculation with N87 cells originated from human gastric cancer in athymic nude mice. When tumor volumes reached approximately 125 $mm^3$, animals were randomly grouped (n=5) based on their tumor size. Five animals in the control group were treated with PBS as a vehicle control. The mice in the test groups were treated with ADCs at a dose of 5 mg/kg in a single bolus injection through a lateral tail vein. Tumor volume was taken twice per week and calculated by the following formula: length×width×height×½.

For DX-111, DX-112, and T-DM1, the results of the in vivo assay are shown in FIG. 1.

The invention claimed is:

1. A ligand-drug conjugate of formula (2):

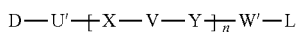

Formula 2 wherein:
D represents a cytotoxic drug;
L represents a cell-binding ligand;
V represents a polar or charged group selected from the group consisting of

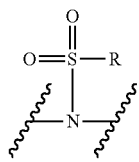

(sulfonamides)

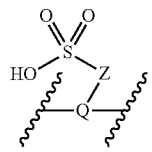

(sulfonic acids),

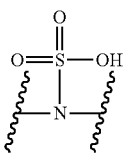

(sulfamic acids), wherein R is H, $C_1$–$C_8$ alkyl, or $NH_2$; Q is CH or N; Z is NH, NH—$(CH_2)_m$, or N($CH_3$)$(CH_2)_m$, wherein m is an integer from 1 to 5, and "⸺" is a site of attachment;

U' represents a covalent linkage selected from the group consisting of a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, and a carbonate linkage;

W' represents a covalent linkage selected from the group consisting of an amide linkage, a carbamate linkage, a urea linkage, a disulfide linkage, a thioether linkage, a thiocarbamate linkage, a dithiocarbamate linkage, and a thioester linkage;

X represents a component composed of one, two, or three methylene units optionally substituted with an alkyl, halo, hydroxyl, or alkoxy group;

Y represents a component composed of one, two, or three methylene units optionally substituted with an alkyl, halo, hydroxyl, or alkoxy group;

n is an integer from 1 to 100, provided that when n>1, values of each V, X, and Y in the repeating, brackets of Formula (2) are independent and do not have to be identical.

2. The conjugate of claim 1, wherein the cell-binding ligand is an antibody, a single chain antibody, an antibody fragment that selectively binds to a target cell, a monoclonal antibody, a single chain monoclonal antibody, a single chain monoclonal antibody fragment that selectively binds to a target cell, a resurfaced monoclonal antibody, a resurfaced single chain monoclonal antibody, a resurfaced monoclonal antibody fragment that selectively binds to a target cell, a chimeric antibody, a single chain chimeric antibody, a single chain chimeric antibody fragment that selectively binds to a target cell, a humanized monoclonal antibody, a humanized single chain monoclonal antibody, a humanized monoclonal antibody fragment that selectively binds to a target cell, an antibody mimic, a lymphokine, a hormone, or a growth factor.

3. The conjugate of claim 2, wherein the antibody: s trastuzumab, pertuzumab, rituximab, ofatumumab, tositumomab, ibritumomab, oregovomab, edrecolomab, cetuximab, panitumumab, nimotuzumab, brentuximab, gemtuzumab, huMy9-6, etaracizumab, alemtuzumab, epratuzumab, labetuzumab, bivatuzumab, sibrotuzumab, huB4, huC242, huN901, daratumumab, DS6, cixutumumab, 3B7, ONTO 95, or 1-84.

4. The conjugate of claim 1, wherein the cell-binding ligand binds to tumor cells expressing tumor associated antigens, epidermal growth factor receptors (EGFR), astrin-releasing peptide receptor (GRPR), bone morphogenetic protein receptor IB (BMPR1B), folate receptor, metalloreductase STEAP1, sodium-dependent phosphate transport protein 2B (Napi3b or SLC34A2), brevican, ephrin receptors (Ephs), prostate stem cell antigen (PSCA), B cell activating factor of the TNF family receptor (BAFF-R), C—X—C chemokine receptor type 5 (CXC-R5, CD185, or BLR1), HLA class II histocompatibility antigen-DO beta chain (HLA-DOB), P2X purinoceptor 5 (P2X5 or P2RX5), transferrin receptors (TfR), hormone receptors, growth-hormone-releasing hormone receptor (GHRHR), epithelial cell adhesion molecule, gangliosides, FMS-like tyrosine kinase 3 (FLT3), prostate-specific membrane antigen (PSMA), mucin 1 (MUC1), mucin 16 (MUC16 or CA-125), six transmembrane epithelial antigen of prostate (STEAP), carcinoembryonic antigen (CEA), decay accelerating factor (DAF or CD55), folate receptors, mesothelin, cryptic family protein 1B (Cripto), integrins, growth factors, transferrins receptors, transport proteins, homing receptors, endothelial cell--linked antigens, IGF-IR, CanAg, C242 antigens, or CD molecules.

5. The conjugate of claim 1, wherein the cytotoxic drug is a maytansinoid, dolastatin, an auristatin, a calicheamicin, a tubulysin, a mitomycin, an actinomycin, a camptothecin, a vinca alkaloid, an anthracycline, a duocarmycin, or a pyrrolo[2,1-c][1,4]benzodiazepines (PBD).

6. The conjugate of claim 1, wherein the cytotoxic drug is DM1.

7. The conjugate of claim 1, wherein the cytotoxic drug is DM4.

8. The conjugate of claim 1, wherein the cytotoxic drug is MMAF.

9. The conjugate of claim 1, wherein V is —N(SO$_2$OH)—.

10. The conjugate of claim 1, wherein n is an integer from 1 to 50.

11. The conjugate of claim 1, wherein n is an integer from 1 to 10.

12. The conjugate of claim 1, wherein n is 1.

13. The conjugate of claim 1, which is a compound of Compound (52)-(55), or (63):

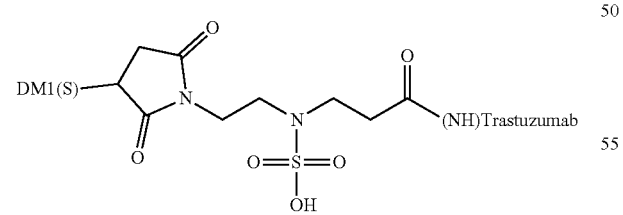
(Compound 52)

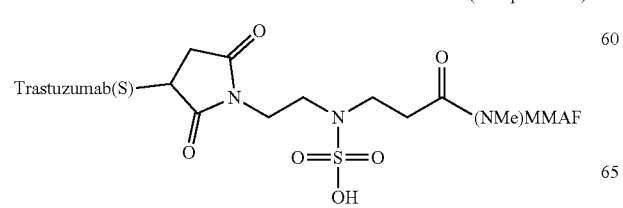
(Compound 53)

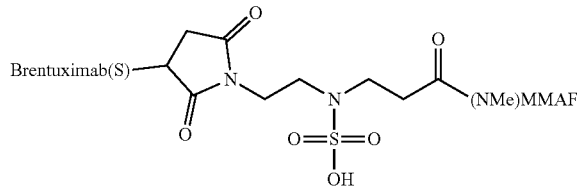
(Compound 54)

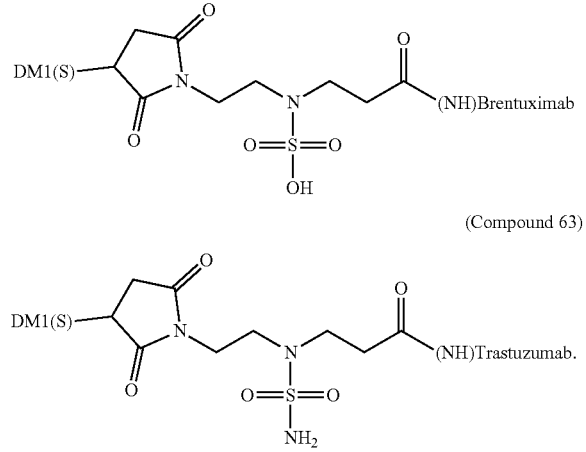
(Compound 55)

(Compound 63)

14. A ligand-drug conjugate of formula (2):

$$D—U'—[X—V—Y]_n—W'—L$$ 
Formula 2 wherein:

D represents a cytotoxic drug;

L represents a cell-binding ligand;

V represents a polar or charged group selected from the group consisting of

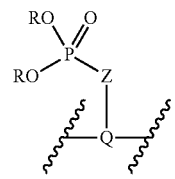

(phosphonates),

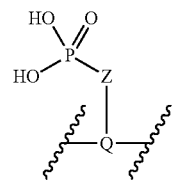

(phosphoric acids),

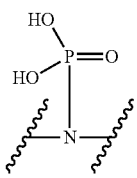

(phosphoramidic acids),

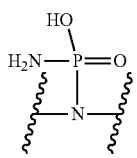

(phosphorodiamidic acids), and

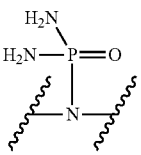

(phosphoric triamides), wherein R is H or $C_1$-$C_8$ alkyl; Q is CH or N L is NH, NH—$(CH_2)_m$, or $N(CH_3)(CH_2)_m$, wherein m is an integer from 1 to 5, and "⸺" is a site of attachment;

U' represents a covalent linkage selected from the group consisting of a disulfide linkage, a thioether linkage, a thioester linkage, an amide linkage, an ester linkage, a carbon-nitrogen linkage, a carbon-carbon linkage, a hydrazine linkage, a hydrazide linkage, a hydrazone linkage, an ether linkage, a carbamate linkage, and a carbonate linkage;

W' represents a covalent linkage selected from the group consisting of an amide linkage, a carbamate linkage, a urea linkage, a disulfide linkage, a thioether linkage, a thiocarbamate linkage, a dithiocarbamate linkage, and a thioester linkage;

X represents a component composed of one, two, or three methylene units optionally substituted with an alkyl, halo, hydroxyl, alkoxy group;

Y represents a component composed of one, two, or three methylene units optionally substituted with an alkyl, halo, hydroxyl, or alkoxy group;

n is an integer from 1 to 100, provided that when n>1, values of each V, X, and Y in the repeating brackets of Formula (2) are independent and do not have to be identical.

15. The conjugate of claim 14, wherein the cell-binding ligand is an antibody, a single chain antibody, an antibody fragment that selectively binds to a target cell, a monoclonal antibody, a single chain monoclonal antibody, a single chain monoclonal antibody fragment that selectively binds to a target cell, a resurfaced monoclonal antibody, a resurfaced single chain monoclonal antibody, a resurfaced monoclonal antibody fragment that selectively binds to a target cell, a chimeric antibody, a single chain chimeric antibody, a single chain chimeric antibody fragment that selectively binds to a target cell, a humanized monoclonal antibody, a humanized single chain monoclonal antibody, a humanized monoclonal antibody fragment that selectively binds to a target cell, an antibody mimic, a lymphokine, a hormone, or a growth factor.

16. The conjugate of claim 15, wherein the antibody is trastuzumab, pertuzumab, rituximab, ofatumumab, tositumomab, ibritumomab, oregovomab, edrecolomab, cetuximab panitumumab, nimotuzumab, brentuximab, gemtuzumab, huMy9-6, etaracizumab, alemtuzumab, epratuzumab, labetuzumab, bivatuzumab, sibrotuzumab, huB4, huC242, huN901, daratumumab, DS6, cixutumumab, 3B7, CNTO 95, or B-B4.

17. The conjugate of claim 14, wherein the cell-binding ligand binds to tumor cells expressing tumor associated antigens, epidermal growth factor receptors (EGFR), astrin-releasing peptide receptor (GRPR), hone morphogenetic protein receptor I B (BMPR1B), folate receptor, metalloreductase STEAP1, sodium-dependent phosphate transport protein 2B (Napi3b or SLC34A2), brevican, ephrin receptors (Ephs), prostate stem cell antigen (PSCA), B cell activating factor of the TNF family receptor (BAFF-R), C—X—C chemokine receptor type 5 (CXC-R5, CD185, or BLR1), MA class II histocompatibility antigen-DO beta chain (HLA-DOB), P2X purinoceptor 5 (P2X5 or P2RX5), transferrin receptors (TfR), hormone receptors, growth-hormone-releasing hormone receptor (GHRHR), epithelial cell adhesion molecule, gangliosides, FMS-like tyrosine kinase 3 (FLT3), prostate-specific membrane antigen (PSMA), mucin 1 (MUC1), mucin 16 (MUC16 or CA-125), six transmembrane epithelial antigen of prostate (STEAP), carcinoembryonic antigen (CEA), decay accelerating factor (DAF or CD55), folate receptors, mesothelin, cryptic family protein 1B (Cripto), integrins, growth factors, transferrins receptors, transport proteins, homing receptors, endothelial cell-linked antigens, IGF-IR, CanAg, C242 antigens, or CD molecules.

18. The conjugate of claim 14, wherein the cytotoxic drug is a maytansinoid, a dolastatin, an auristatin, a calicheamicin, a tubulysin, a mitomycin, an actinomycin, camptothecin, vinca alkaloid, an anthracycline, a duocarmycin, or a pyrrolo[2,1-c][1,4]benzodiazepines (PBD).

19. The conjugate of claim 14, wherein the cytotoxic drug is DM1.

20. The conjugate of claim 14, wherein the cytotoxic drug is M14.

21. The conjugate of claim 14, wherein the cytotoxic drug is MMAF.

22. The conjugate of claim 14, wherein V is —N[PO(OH)$_2$]—.

23. The conjugate of claim 14, wherein n is an integer from 1 to 50.

24. The conjugate of claim 14, wherein n is an integer from 1 to 10.

25. The conjugate of claim 14, wherein n is 1.

26. The conjugate of claim 14, which is a compound of compound (56)-(59), (61) or (62):

(Compound 56)

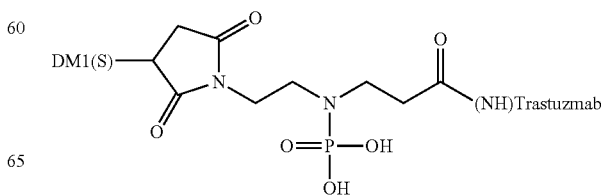

-continued
(Compound 57)
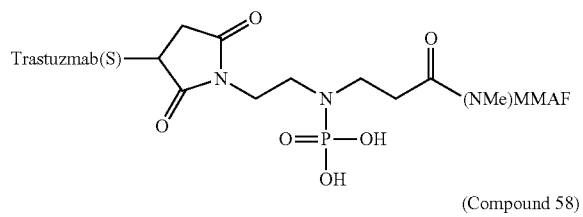
(Compound 58)
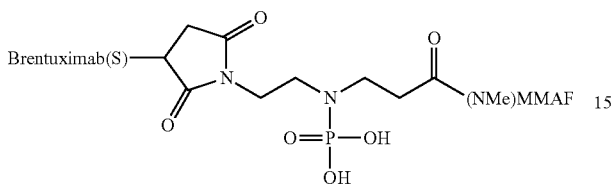
(Compound 59)
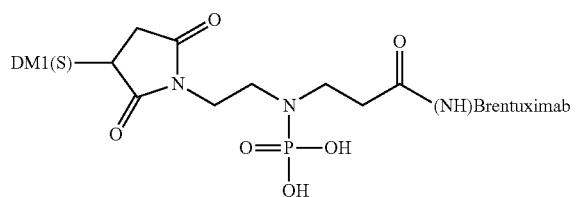
-continued
(Compound 61)
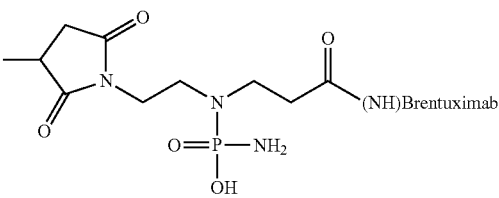
(Compound 62)
DM1(S)— [structure] —(NH)Trastuzmab.
* * * * *